(12) United States Patent
Klebsattel et al.

(10) Patent No.: US 7,402,733 B2
(45) Date of Patent: Jul. 22, 2008

(54) TRANSGENIC EXPRESSION CASSETTES FOR EXPRESSING NUCLEIC ACIDS IN NON-REPRODUCTIVE FLORAL TISSUES OF PLANTS

(75) Inventors: Martin Klebsattel, Quedlinburg (DE); Ulrich Keetman, Quedlinburg (DE); Karin Herbers, Quedlinburg (DE); Ralf Flachmann, Quedlinburg (DE); Matt Sauer, Quedlinburg (DE); Heike Hillebrand, Mannheim (DE)

(73) Assignee: SunGene GmbH & Co. KGaA (DE)

( * ) Notice: Subject to any disclaimer, the term of this patent is extended or adjusted under 35 U.S.C. 154(b) by 95 days.

(21) Appl. No.: 10/526,411

(22) PCT Filed: Aug. 29, 2003

(86) PCT No.: PCT/EP03/09594

§ 371 (c)(1),
(2), (4) Date: Mar. 2, 2005

(87) PCT Pub. No.: WO2004/027070

PCT Pub. Date: Apr. 1, 2004

(65) Prior Publication Data

US 2006/0168695 A1 Jul. 27, 2006

(30) Foreign Application Priority Data

Sep. 3, 2002 (DE) ................ 102 41 124

(51) Int. Cl.
*C12N 15/82* (2006.01)
*C12N 15/87* (2006.01)
*A01H 5/00* (2006.01)
*A01H 5/10* (2006.01)

(52) U.S. Cl. ................ 800/287; 800/278; 800/298; 800/295; 536/24.1; 435/320.1

(58) Field of Classification Search ........................ None
See application file for complete search history.

(56) References Cited

U.S. PATENT DOCUMENTS 6,320,102 B1 * 11/2001 Harada et al. ............... 800/287
2006/0194274 A1 8/2006 Flachmann et al.

FOREIGN PATENT DOCUMENTS

| AU | 740911 | 4/1999 |
| EP | 0 984 064 | 3/2000 |
| WO | WO-92/16635 | 10/1992 |
| WO | WO-98/22593 | 5/1998 |
| WO | WO-99/15679 | 4/1999 |

OTHER PUBLICATIONS

Takatsuji et al 1991 The EMBO Journal 11:241-249.*
Axelos et al 1989 Mol Gen Genet 219:106-112.*
Axelos et al Genbank Accession ATU63815.*
Roessler et al 1993 The Journal of Biochemistry 268:19254-19259.*
Koes et al 1986 Nucleic Acids Research 14:5229-5239.*
Hill, Theresa A. et al., "Discrete Spatial and Temporal cis-acting Elements Regulate Transcription of The *Arabidopsis* Floral Homeotic gene *APETALA3*." Development (Cambridge), vol. 125, Nr. 9, May 1998, pp. 1711-1721.
Takatsuji Hiroshi et al., "A New Family of Zinc Finger Proteins in Petunia: Structure, DNA Sequence Recognition, and Floral Organ-Specific Expression," The Plant Cell, vol. 6, Nr. 7, Jul. 1994, pp. 947-958.
Town, C.D. et al., "*Arabidopsis thaliana* chromosome 1, complete sequence." GenBank Accession No. NC_003070.2, Region 23069430-23070871, Jan. 10, 2002.
Town, C.D. et al. "*Arabidopsis thaliana* chromosome 1 CHR1v07142002 genomic sequence." GenBank Accession No. NM_104992.1, Aug. 20, 2002.
"*Arabidopsis thaliana* chromosome 3, complete sequence." GenBank Accession No. NC_003074, Region: complement 327462-329029, Feb. 19, 2004.
"*Arabidopsis thaliana* short-chain dehydrogenase/reductase (SDR) family protein (Al3g01980) mRNA, complete cds." GenBank Accession No. NM_111064, Feb. 19, 2004.
"*Arabidopsis thaliana* chromosome III BAC F1C9 genomic sequence, complete sequence", Database GenBank, Accession No. AC011664, Oct. 30, 2002.
"*Arabidopsis thaliana* chromosome III BAC F28J7 genomic sequence, complete sequence", Database GenBank, Accession No. AC010797, Oct. 30, 2002.

* cited by examiner

*Primary Examiner*—Phuong Bui
*Assistant Examiner*—Brent T Page
(74) *Attorney, Agent, or Firm*—Connolly Bove Lodge & Hutz LLP

(57) ABSTRACT

The invention relates to methods for the targeted transgenic expression of nucleic acid sequences in nonreproductive floral tissues of plants, and to transgenic expression cassettes and expression vectors which comprise promoters having an expression specificity for nonreproductive tissues of the flower. The invention further relates to organisms (preferably plants) transformed with these transgenic expression cassettes or expression vectors, to cultures, parts or propagation material derived therefrom, and to the use of the same for producing human and animal foods, seeds, pharmaceuticals or fine chemicals.

14 Claims, 14 Drawing Sheets

Figure 1:
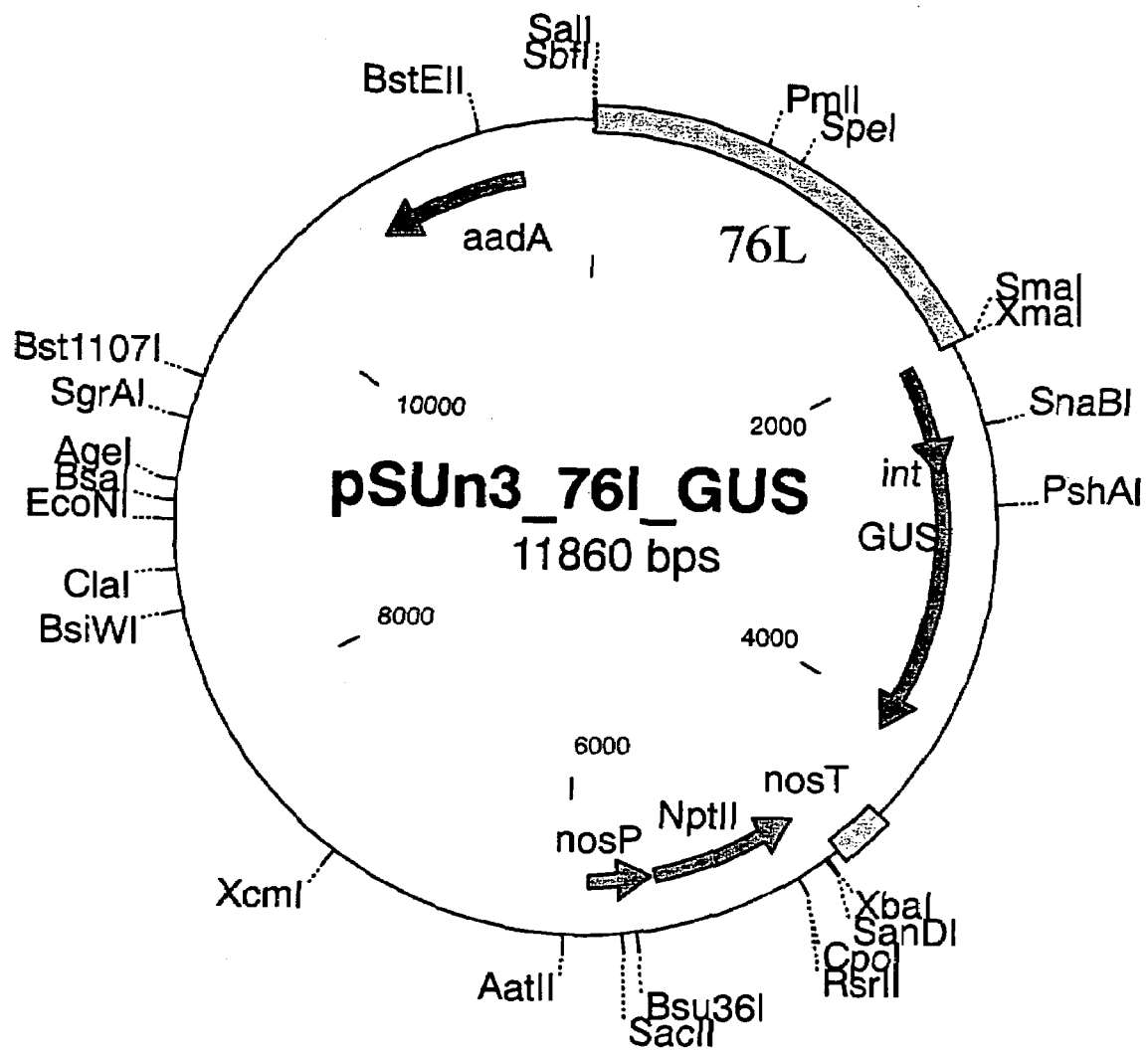

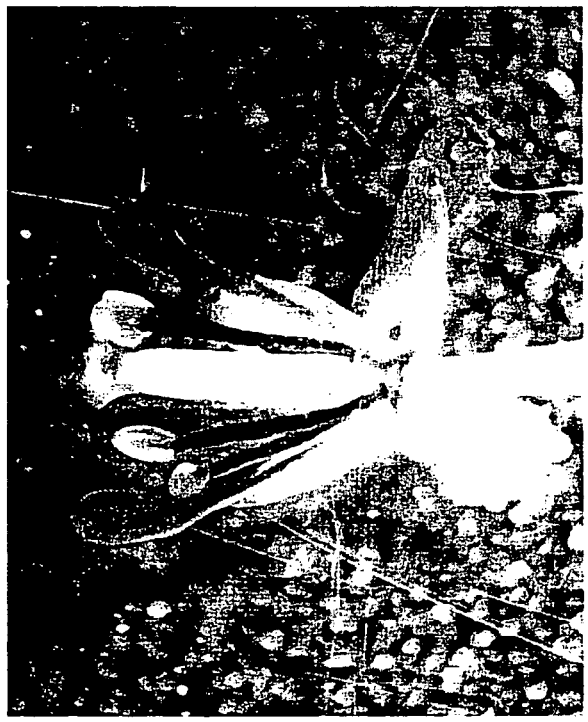
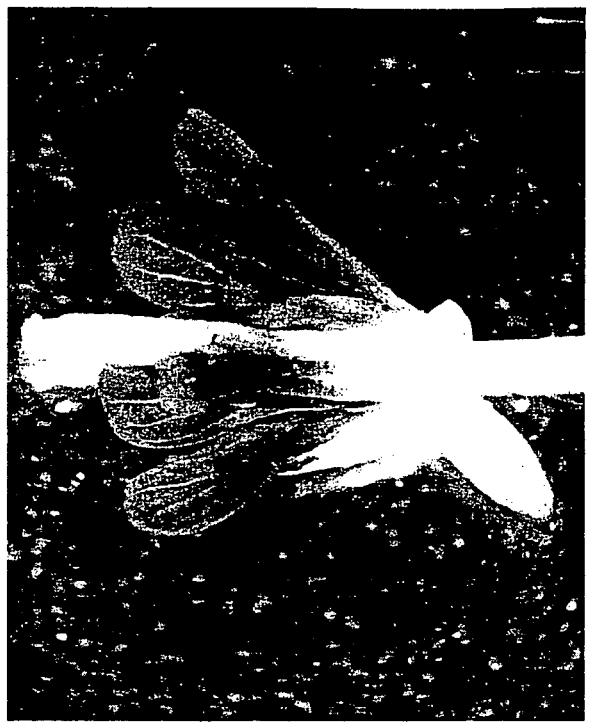
Fig. 6

Fig. 7

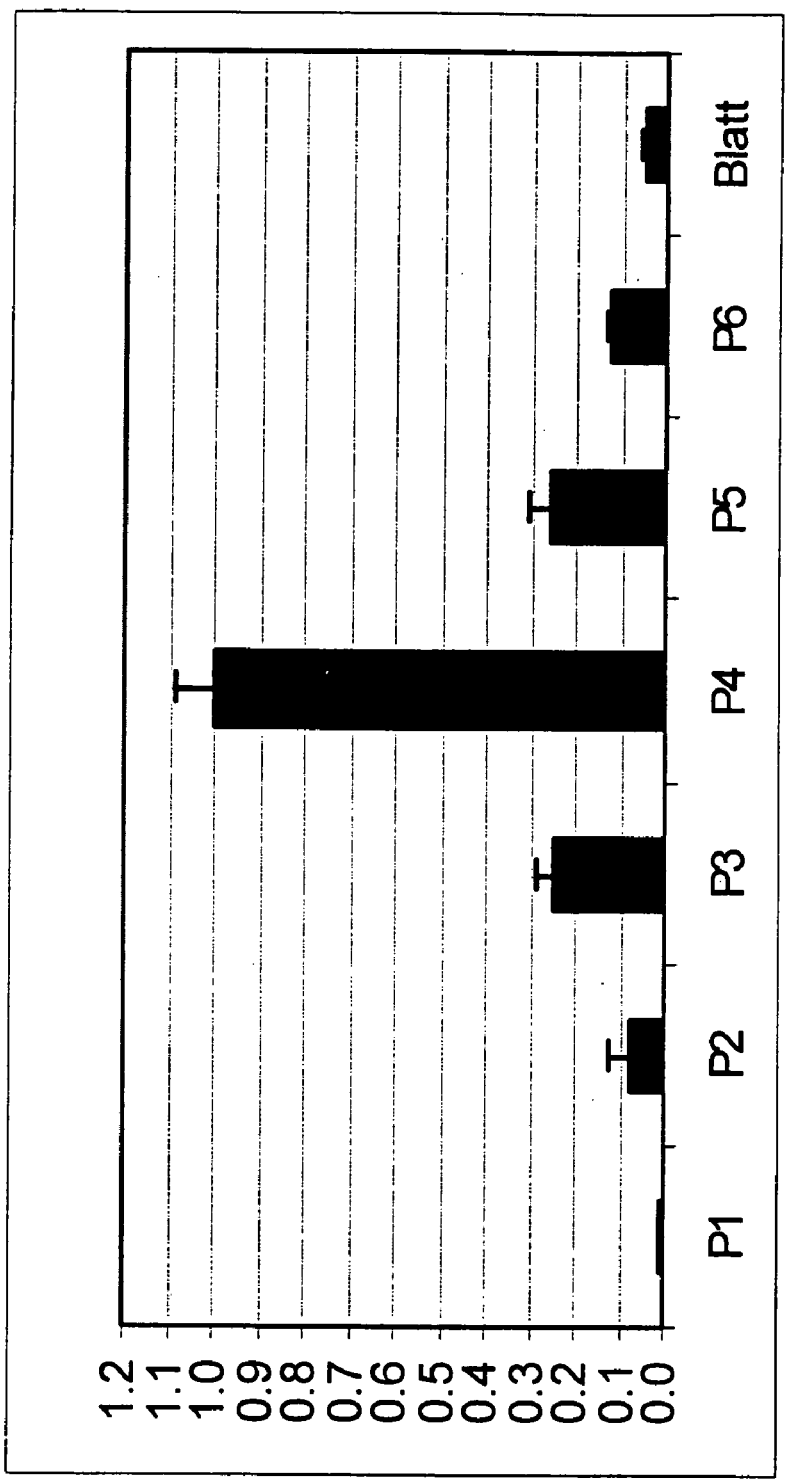
Fig. 11

```
At3g01980   (1)  NCFIKSYFGKMENPAKRVLMTSNGDEVSRNIAFHLAKHGCKLVMMGNEGSLRSIVDKIRDSIEGAFPADVIALDME   76
Brassica H2 (1)  ----------------NGDEVSRNIAIQLAKHGCRLVLMGNEASLRSTVDYIRVSVDGAFPVELIGADME
Brassica H3 (1)  EFSGRRFRTTLNLMANKVLMTDNGDQVSRNIAIQLAKHGCRLVLMGNEASLRSTVDYIRFSDDGAFPVELIGADME
Consensus   (1)       K F   L    A  KVLMT NGDEVSRNIAIQLAKHGCRLVLMGNEASLRSTVDYIR SIDGAFPVELIGADME At3g01980   (77) SDSEVAFHAAVQKAWELSGHFEDAFLNSYTYQGKVQDILQVSQDEFHRITKINLTAPWFLLKAVATRMKDHGSGGSI  152
Brassica H2 (55) ADSEEDFYVAVQKAWTRLGSLDAFVNCCTYQGKMQDILRVSEDEFKKITRINLTATWFILKAVASMMKENGTGGSI
Brassica H3 (77) ADSEEDFYVAVQTAWTRLGSLDAFVNCCTYQGKMQDILRVSEDEFKKITRINLTATWFILKAVASM---------
Consensus   (77) ADSEEDFYVAVQKAWTRLGSLDAFVNCCTYQGKMQDILRVSEDEFKKITRINLTATWFILKAVASMMKD GSGGSI
```

Fig. 12

```
                    1                                                                              82
At1g63140   (1)    KYRTVETGDNIGSRKTERVYAAEPVCTFFLNRGDGLGSLATLFMVLQGEVCMKPWEHLKDMILEGKDAFTSAHGMRFFELIG
Brassica H4 (1)    ---RRFRGENNLTGKIQMVYAAEPVCTLFLKHGHESGSLMSLFMVHHSQVFFETWTHLKDLIQEGKDTFISAHGMRIFEYIG
Brassica H5 (1)    ------------AEPVCTLFLTRGDDSGTHKSLFMLLNSQVFFKTWDNLKGVIQEGKDAFSSAHGMPLFEYIG
Consensus   (1)             GDN  S  K   VYAAEPVCTLFL RGDDSGSL SLFMVLNSQVFFKTWDHLKDLIQEGKDAFSSAHGMRIFEYIG
                   83                                                                              164
At1g63140   (83)   SNEQFAEMFNRAMSEASTLIMKKVLEVYKGFEDVNTLVDGGGIGTIIGQVTSKYPHIKGINFDLASVLAHAPFNKGVEHVS
Brassica H4 (80)   LNEQFACMFNHAMSESSTMIMKKILEVYRGFEDIKTLVDGGLGTTLNLVTSKYPHIRV--FRLN---------------
Brassica H5 (62)   LDEQFAGMFNHAMAESSTIIMKKILEVYRGFEDVNTLVDIGGLGTVLNLVTSKYPQIKGINFDLTMVLANAPSYPGV----
Consensus   (83)   LNEQFA MFNHAMSESSTIIMKKILEVYRGFEDVNTLVDIGGGLGTILNLVTSKYPHIKGINFDL   VLA AP    GV
```

Fig. 13

US 7,402,733 B2

TRANSGENIC EXPRESSION CASSETTES FOR EXPRESSING NUCLEIC ACIDS IN NON-REPRODUCTIVE FLORAL TISSUES OF PLANTS

RELATED APPLICATIONS

This application is a national stage application (under 35 U.S.C. 371) of PCT/EP2003/009594 filed Aug. 29, 2003, which claims benefit of German application 102 41 124.7 filed Sep. 3, 2002.

The invention relates to methods for the targeted transgenic expression of nucleic acid sequences in nonreproductive floral tissues of plants, and to transgenic expression cassettes and expression vectors which comprise promoters having an expression specificity for nonreproductive floral tissues of plants. The invention further relates to organisms (preferably plants) transformed with these transgenic expression cassettes or expression vectors, to cultures, parts or propagation material derived therefrom, and to the use of the same for producing human and animal foods, seeds, pharmaceuticals or fine chemicals.

The aim of biotechnological operations on plants is to produce plants with advantageous novel properties, for example for increasing the agricultural productivity, for increasing the quality of human foods or for producing particular chemicals or pharmaceuticals (Dunwell J M (2000) J Exp Bot 51 Spec No:487-96). A basic precondition for transgenic expression of particular genes is the provision of plant-specific promoters. Promoters are important tools in plant biotechnology for controlling the expression of particular genes in a transgenic plant and thus achieving particular traits of the plant.

Various plant-specific promoters are known, for example constitutive promoters such as the promoter of the *Agrobacterium* nopaline synthase, the TR dual promoter or the promoter of the cauliflower mosaic virus (CaMV) 35S transcript (Odell et al. (1985) Nature 313:810-812). A disadvantage of these promoters is that they are constitutively active in virtually all tissues of the plant. Targeted expression of genes in particular plant parts or at particular times of development is not possible with these promoters.

Promoters having specificities for various plant tissues such as anthers, ovaries, flowers, leaves, stalks, roots, tubers or seeds have been described. The stringency of the specificity and the expression activity of these promoters varies widely.

The flower of plants serves for sexual reproduction of flowering plants. The flowers of plants—especially the petals—frequently accumulate large amounts of secondary plant products such as, for example, terpenes, anthocyans, carotenoids, alkaloids and phenylpropanoids, which serve as scents, defensive substances or as colorants in the flower. Many of these substances are of commercial interest. In addition, the flower bud and the flower of the plant is a sensitive organ, especially to stress factors such as cold.

The *Arabidopsis thaliana* gene locus At3g01980 (GenBank Acc.-No.: NC_003074; *Arabidopsis thaliana* chromosome 3; base pairs: complement 327677 to 329029) encodes a putative dehydrogenase (derived cDNA: GenBank Acc.-No: NM_111064; SEQ ID NO: 11). The *Arabidopsis thaliana* gene locus At1g63140 (GenBank Acc.-No: NC_003070.2; *Arabidopsis thaliana* chromosome 1; base pairs 23069430 to 23070871) encodes a putative caffeic acid o-methyltransferase (derived cDNA: GenBank Acc.-No: NM_104992.1; SEQ ID NO: 13). The precise function, transcription and the expression patterns of these genes are not described.

Flower-specific promoters such as, for example, the phytoene synthase promoter (WO 92/16635), the promoter of the P-rr gene (WO 98/22593) or the promoter of the APETALA3 gene (Hill T A et al. (1998) Development 125:1711-1721) are known. However, all these promoters have one or more disadvantages which are prejudicial to wide use:

1) within the flower they are specific for one or more flower tissues and do not guarantee expression in all tissues of the flower.
2) they are—as in the example of the APETALA3 gene which is involved in flower development—highly regulated during flower development and are not active in all phases of flower development.
3) they occasionally show strong secondary activities in other plant tissues. Thus, the known promoters (such as, for example, the APETALA3 promotor) show in most cases an activity in seeds, anthers and the ovaries of the flower, which constitute sensitive floral organs which are directly involved in the plants' reproduction. Expression here is in many cases unnecessary and disadvantageous since it may interfere with the plants' reproduction. Moreover, the expressed gene product can be dispersed in an undesired manner by seeds and pollen in the air. For the purposes of a biotechnological exploitation of transgenic plants, this is largely to be avoided.

Despite the large number of known plant promoters, no promoter with a specificity for the plant flower which essentially lacks expression in the pollens and ovaries, i.e. which is only active in the nonreproductive tissues, has been identified to date, nor are any promoters known which, in addition to having the abovementioned specificity, are active essentially during all of the floral development.

It is therefore an object to provide methods and suitable promoters for the targeted, transgenic expression of nucleic acids into the nonreproductive floral tissues. We have found that this object is achieved by providing the promoters of the genes with the gene locus names At3g01980 (hereinbelow "76L" promoter; SEQ ID NO: 1) and At1g63140 (hereinbelow "84L" promoter; SEQ ID NO: 2) from *Arabidopsis thaliana*. These promoters show expression in all floral organs with the exception of the pollen and the ovaries. This expression pattern can be observed in the flower bud, the flower and the wilting flower.

A first aspect of the invention relates to methods for the targeted transgenic expression of nucleic acid sequences in nonreproductive floral tissues of plants, comprising the following steps:

I. introduction of a transgenic expression cassette into plant cells, wherein the transgenic expression cassette comprises at least the following elements
   a) at least one promoter sequence selected from the group of sequences consisting of
      i) the promoter sequences of SEQ ID NO: 1 or 2 and
      ii) functional equivalents of the promoter sequences of SEQ ID NO: 1 or 2 with essentially the same promoter activity as a promoter of SEQ ID NO: 1 or 2 and
      iii) functional equivalent fragments of the sequences of i) or ii) with essentially the same promoter activity as a promoter of SEQ ID NO: 1 or 2, and
   b) at least one further nucleic acid sequence, and
   c) optionally further genetic control elements,
   wherein at least one promoter sequence and one further nucleic acid sequence are functionally linked together, and the further nucleic acid sequence is heterologous in relation to the promoter sequence, and II. selection of transgenic cells which comprise said expression cassette stably integrated into the genome, and III. regeneration of complete plants from said transgenic cells, wherein at least one of the further nucleic acid sequences is expressed essentially in all nonreproductive floral tissues, but essentially not in the pollen and the ovaries.

A further aspect relates to transgenic expression cassettes as, for example, can be employed in the method of the invention. The transgenic expression cassettes preferably comprise for the targeted transgenic expression of nucleic acid sequences in nonreproductive floral tissues of plants, a) at least one promoter sequence selected from the group of sequences consisting of
 i) the promoter sequences of SEQ ID NO: 1 or 2 and
 ii) functional equivalents of the promoter sequences of SEQ ID NO: 1 or 2 with essentially the same promoter activity as a promoter of SEQ ID NO: 1 or 2 and
 iii) functionally equivalent fragments of the sequences of i) or ii) with essentially the same promoter activity as a promoter of SEQ ID NO: 1 or 2, and
b) at least one further nucleic acid sequence, and
c) optionally further genetic control elements, wherein at least one promoter sequence and one further nucleic acid sequence are functionally linked together, and the further nucleic acid sequence is heterologous in relation to the promoter sequence.

The expression cassettes of the invention may comprise further genetic control sequences and/or additional functional elements.

It is possible and preferred for the transgenic expression cassettes to make possible, through the nucleic acid sequence to be expressed transgenically, the expression of a protein encoded by said nucleic acid sequence and/or the expression of a sense-RNA, antisense-RNA or double-stranded RNA encoded by said nucleic acid sequence.

A further aspect of the invention relates to transgenic expression vectors which comprise one of the expression cassettes of the invention.

A further aspect of the invention relates to transgenic organisms which comprise one of the expression cassettes or expression vectors of the invention. The organism can be selected from the group consisting of bacteria, yeasts, fungi, nonhuman animal and plant organisms or of cells, cell cultures, parts, tissues, organs or propagation material derived therefrom, and the organism is preferably selected from the group of agricultural crop plants.

A further aspect of the invention therefore relates to the use said transgenic organisms or cells, cell cultures, parts, tissues, organs or propagation material derived therefrom to produce human and animal foods, seeds, pharmaceuticals or fine chemicals, where the fine chemicals are preferably enzymes, vitamins, amino acids, sugars, saturated or unsaturated fatty acids, natural or synthetic flavorings, aromatizing substances or colorants. The invention further includes methods for producing said human and animal foods, seeds, pharmaceuticals or fine chemicals employing the trangenic organisms of the invention or cells, cell cultures, parts, tissues, organs or propagation material derived therefrom.

The transgenic expression cassettes of the invention are particularly advantageous for the following reasons:

a) they impart selective expression in nonreproductive tissues of the flower bud and the flower of plants and make numerous applications possible, such as, for example, resistance to stress factors such as cold or targeted synthesis of secondary plant products. Expression takes place throughout the period of flower bud and flower development.

b) they show no expression in reproductive tissues (such as pollen or ovaries), whereby interference with the reproduction and spreading of the transgenic protein by pollen or seeds in the air is avoided.

The transgenic expression cassettes according to the invention, and the transgenic expression vectors and transgenic organisms derived from them, may comprise functional equivalents of the promoter sequences described under SEQ ID NO: 1 or 2.

The promoter activity of a functionally equivalent promoter is referred to as being "essentially the same" when the transcription of a particular nucleic acid sequence to be expressed transgenically under the control of said functionally equivalent promoter under otherwise unchanged conditions shows a targeted expression in essentially all nonreproductive floral tissues, with essentially no expression in the pollen and ovaries.

"Flower" generally means a shoot of limited growth whose leaves have been transformed into reproductive organs. The flower consists of various "floral tissues" such as, for example, the sepals, the petals, the stamens or the carpels. Androecium is the term used for the totality of stamens in the flower. The stamens are located within the circle of petals and sepals. A stamen is composed of a filament and of an anther located at the end. The latter in turn is divided into two thecae which are connected together by a connective. Each theca consists of two pollen sacs in which the pollen is formed.

"Nonreproductive floral tissue" refers to all tissues of the flower except for the pollen and the ovaries.

"Essentially all nonreproductive floral tissues" means with regard to the nonreproductive floral tissues that some of these tissues, either in total or at specific points in time of their development, may display no substantial expression, where these tissues however amount to preferably less than 20% by weight, preferably less than 10% by weight, especially preferably less than 5% by weight, very especially preferably less than 1% by weight of the total weight of the nonreproductive floral tissues.

"Targeted" means in relation to the expression in nonreproductive floral tissues preferably that the expression under the control of one of the promoters of the invention in the nonreproductive floral tissues is at least ten times, particularly preferably at least fifty times, very particularly preferably at least one hundred times that of another tissue such as, for example, the pollen or the ovaries or a nonfloral tissue, such as the leaves.

The fact that the promoters according to the invention "show essentially no expression in the pollen and ovaries" preferably means that the statistical mean of the expression over all reproductive floral tissues is at most 10%, preferably at most 5%, most preferably at most 1% that of the statistical mean of the expression over all nonreproductive floral tissues under identical conditions.

Preferably, the expression within the nonreproductive floral tissues is essentially constant. "Essentially constant" in this context preferably means that the standard deviation of the expression between the individual nonreproductive floral tissues relative to the statistical mean of the expression over all nonreproductive floral tissues is less than 50%, preferably 20%, especially preferably 10%, very especially preferably 5%.

Preferably, the expression within at least one particular nonreproductive floral tissue is essentially constant over all developmental stages of the flower. "Essentially constant" in this context preferably means that the standard deviation of the expression between the individual points in time of the development of the particular nonreproductive floral tissue relative to the statistical mean of the expression over all points in time of the development is less than 50%, preferably 20%, especially preferably 10%, very especially preferably 5%.

The nucleic acid sequences in functional linkage with the test promoter which are preferably employed for estimating the level of expression are those which code for easily quantifiable proteins. Very particular preference is given in this connection to reporter proteins (Schenborn E, Groskreutz D. (1999) Mol Biotechnol 13(1): 29-44) such as the green fluorescence protein (GFP) (Chiu W L et al. (1996) Curr Biol 6:325-330; Leffel S M et al. (1997) Biotechniques 23(5):912-8), chloramphenicol transferase, luciferase (Millar et al. (1992) Plant Mol Biol Rep 10:324-414), β-glucuronidase or β-galactosidase. Very particular preference is given to β-glucuronidase (Jefferson et al. (1987) EMBO J 6:3901-3907).

"Conditions which are otherwise unchanged" means that the expression initiated by one of the transgenic expression cassettes to be compared is not modified by combination with additional genetic control sequences, for example enhancer sequences. Unchanged conditions further means that all general conditions such as, for example, plant species, stage of development of the plants, culture conditions, assay conditions (such as buffer, temperature, substrates etc.) are kept identical between the expressions to be compared.

"Transgenic" means—for example in relation to an expression cassette (or to an expression vector or transgenic organism comprising the former) all those constructions which have originated by recombinant methods in which either a) the promoter of SEQ ID NO: 1 or 2 or a functional equivalent thereof or a functional equivalent part of the above, or b) a further nucleic acid sequence which is functionally linked with a), or c) (a) and (b)

are not in their natural genetic environment or have been modified by recombinant methods, it being possible for the modification to be, for example, a substitution, addition, deletion, inversion or insertion of one or more nucleotide residues. The promoter sequence of the invention (e.g. the sequence as shown in SEQ ID NO: 1, 2, 3 or 4) comprised in the expression cassettes is preferably heterologous in relation to the further nucleic acid sequence which is to be expressed transgenically and is functionally linked thereto. "Heterologous" means in this connection that the further nucleic acid sequence does not code for the gene which is naturally under the control of said promoter.

"Natural genetic environment" means the natural chromosomal locus in the original organism or the presence in a genomic library. In the case of a genomic library, the natural, genetic environment of the nucleic acid sequence is preferably still retained at least in part. The environment flanks the nucleic acid sequence at least on one side and has a sequence length of at least 50 bp, preferably at least 500 bp, particularly preferably at least 1000 bp, very particularly preferably at least 5000 bp. A naturally occurring expression cassette—for example the naturally occurring combination of the promoter of a gene coding for a protein as shown in SEQ ID NO: 12 or 14 or a functional equivalent thereof with its corresponding coding sequences becomes a trangenic expression construct when the latter is modified by unnatural, synthetic ("artificial") methods such as, for example, a mutagenesis. Appropriate methods are described (U.S. Pat. No. 5,565,350; WO 00/15815; see also above).

"Transgenic" means in relation to an expression ("transgenic expression") preferably all expressions caused by use of a transgenic expression cassette, transgenic expression vector or transgenic organism—complying with the definitions given above.

Functional equivalents of a promoter of SEQ ID NO: 1 or 2 in particular means natural or artificial mutations of a promoter of SEQ ID NO: 1 or 2 and homologous sequences from other organisms, preferably from plant organisms, which have essentially the same promoter activity as one of the promoters of SEQ ID NO: 1 or 2.

Functional equivalents also comprises all those sequences which are derived from the complementary counterstrand of the sequences defined by SEQ ID NO: 1 or 2 and have essentially the same promoter activity.

Functional equivalents to the promoters of SEQ ID NO: 1 or 2 preferably comprise those sequences which a) have essentially the same promoter activity as one of the promoters of SEQ ID NO: 1 or 2 and b) have a homology of at least 50%, preferably 70%, more preferably at least 80%, particularly preferably at least 90%, very particularly preferably at least 95%, most preferably 99%, with the sequence of one of the promoters of SEQ ID NO: 1 or 2, wherein the homology extends over a length of at least 100 base pairs, preferably at least 200 base pairs, particularly preferably of at least 300 base pairs, very particularly preferably of at least 400 base pairs, most preferably of at least 500 base pairs.

It is possible in this connection for the level of expression of the functional equivalents to differ both downwards and upwards from a comparison value. Preference is given in this connection to the sequences whose level of expression, measured on the basis of the transcribed mRNA or the subsequently translated protein, under conditions which are otherwise unchanged differs quantitatively by not more than 50%, preferably 25%, particularly preferably 10%, from a comparison value obtained with the promoters described by SEQ ID NO: 1 or 2. Particularly preferred sequences are those whose level of expression, measured on the basis of the transcribed mRNA or the subsequently translated protein, under conditions which are otherwise unchanged exceeds quantitatively by more than 50%, preferably 100%, particularly preferably 500%, very particularly preferably 1000%, a comparison value obtained with the promoter described by SEQ ID NO: 1 or 2.

Examples of promoter sequences employed in the transgenic expression cassettes or transgenic expression vectors of the invention can easily be found for example in various organisms whose genomic sequence is known, such as, for example, *Arabidopsis thaliana, Brassica napus, Nicotiana tabacum, Solanum tuberosum, Helianthium annuus, Linum sativum*, by making homology comparisons in databases. A possible and preferred starting point for this is the coding regions of the genes whose promoters are described by SEQ ID NO: 1 or 2. Starting from, for example, the cDNA sequences of these genes described by SEQ ID NO: 11 or 13 or the protein sequences derived therefrom and described by SEQ ID NO: 12 or 14 it is possible easily to identify, in a manner familiar to the skilled worker, the corresponding homologous genes in other plant species by screening databases or gene libraries (using appropriate gene probes).

In a preferred embodiment of the invention, functional equivalents of the promoter described by SEQ ID NO: 1 comprise all those promoters which are located in a plant organism in the 5' direction upstream of a genomic sequence which encodes a protein with at least 60%, preferably at least 80%, especially preferably at least 90%, most preferably at least 95% homology with the protein of SEQ ID NO: 12, wherein said promoters constitute the natural promoter of said genomic sequence. Especially preferably, functional equivalents of the promoter described by SEQ ID NO: 1 comprise all those promoters which are located in a plant organism in the 5' direction upstream of a genomic sequence which encodes a nucleic acid sequence whose derived cDNA has at least 60%, preferably at least 80%, especially preferably at least 90%, most preferably at least 95% homology with the nucleic acid sequence as shown in SEQ ID NO: 11, wherein said promoters constitute the natural promoter of said genomic sequence. Preferred promoters comprise a sequence region of least 250 base pairs, preferably at least 500 base pairs, particularly preferably 1000 base pairs, most preferably at least 2000 base pairs, in the 5' direction calculated from the ATG start codon of said genomic sequences. Functional equivalents of the promoter described by SEQ ID NO: 1 are particularly preferably all promoters which are located in a plant organism in the 5' direction upstream of a genomic sequence which encodes a protein which comprises at least one of the following sequence motifs:

```
1. NGD(E/Q)VSRNIA           (SEQ ID NO: 23)
2. LAKHGC(R/K)LV             (SEQ ID NO: 24)
3. MGNEXSLRSXVDXIR           (SEQ ID NO: 25)
4. TYQGKXQDILXVS(Q/E)DEF     (SEQ ID NO: 26)
5. IT(K/R)INLTAXWFXLKAVA     (SEQ ID NO: 27)
```

Very particularly preferred functional equivalents of the promoter described by SEQ ID NO: 1 are those promoters which are located in a plant organism in the 5' direction upstream of a genomic sequence which encodes a protein, wherein said protein comprises at least one of the following sequences:
1. the homologous sequence (H2) from oilseed rape as shown in SEQ ID NO: 16
2. the homologous sequence (H3) from oilseed rape as shown in SEQ ID NO: 18

Most preferred functional equivalents of the promoter described by SEQ ID NO: 1 are those promoters which are located in a plant organism in the 5' direction upstream of a genomic sequence which encodes a nucleic acid sequence whose derived cDNA comprises at least one of the following sequences:
1. the homologous sequence (H2) from oilseed rape as shown in SEQ ID NO: 15
2. the homologous sequence (H3) from oilseed rape as shown in SEQ ID NO: 17

In a preferred embodiment of the invention, functional equivalents of the promoter described by SEQ ID NO: 2 comprise all those promoters which are located in a plant organism in the 5' direction upstream of a genomic sequence which encodes a protein with at least 60%, preferably at least 80%, especially preferably at least 90%, most preferably at least 95% homology with the protein of SEQ ID NO: 14, wherein said promoters constitute the natural promoter of said genomic sequence. Especially preferably, functional equivalents of the promoter described by SEQ ID NO: 2 comprise all those promoters which are located in a plant organism in the 5' direction upstream of a genomic sequence which encodes a nucleic acid sequence whose derived cDNA has at least 60%, preferably at least 80%, especially preferably at least 90%, most preferably at least 95% homology with the nucleic acid sequence as shown in SEQ ID NO: 13, wherein said promoters constitute the natural promoter of said genomic sequence. Preferred promoters comprise a sequence region of least 250 base pairs, preferably at least 500 base pairs, particularly preferably 1000 base pairs, most preferably at least 2000 base pairs, in the 5' direction calculated from the ATG start codon of said genomic sequences. Functional equivalents of the promoter described by SEQ ID NO: 2 are particularly preferably all promoters which are located in a plant organism in the 5' direction upstream of a genomic sequence which encodes a protein which comprises at least one of the following sequence motifs:

```
1. AEPVCTXFL                 (SEQ ID NO: 28)
2. EGKDXFXSAHGMXXFE          (SEQ ID NO: 29)
3. EQFAXMFNXAM               (SEQ ID NO: 30)
4. ATXIMKK(V/I)LEVY(K/R)GFED (SEQ ID NO: 31)
5. TLVD(V/I)GGGXGT           (SEQ ID NO: 32)
```

Very particularly preferred functional equivalents of the promoter described by SEQ ID NO: 2 are those promoters which are located in a plant organism in the 5' direction upstream of a genomic sequence which encodes a protein, wherein said protein comprises at least one of the following sequences:
1. the homologous sequence (H4) from oilseed rape as shown in SEQ ID NO: 20
2. the homologous sequence (H5) from oilseed rape as shown in SEQ ID NO: 22

Most preferred functional equivalents of the promoter described by SEQ ID NO: 2 are those promoters which are located in a plant organism in the 5' direction upstream of a genomic sequence which encodes a nucleic acid sequence whose derived cDNA comprises at least one of the following sequences:
1. the homologous sequence (H4) from oilseed rape as shown in SEQ ID NO: 19
2. the homologous sequence (H5) from oilseed rape as shown in SEQ ID NO: 21

A further subject of the invention therefore relates to polypeptides comprising an amino acid sequence as shown in SEQ ID NO: 16, 18, 20 or 22 and the nucleic acid sequences encoding them, preferably the sequences comprising a sequence as shown in SEQ ID NO: 15, 17, 19 or 21 or the sequences derived therefrom the result of degeneracy of the genetic code.

A further aspect of the invention relates to the use of at least one nucleic acid sequence or of a part thereof in methods for identifying and/or isolating promoters of genes which code for said nucleic acid sequence, wherein said nucleic acid sequence encodes an amino acid sequence comprising at least one sequence as shown in SEQ ID NO: 23, 24, 25, 26, 27, 28, 29, 30, 31 or 32 or a variation indicated for these sequences. Said nucleic acid sequence preferably codes for an amino acid sequence comprising a sequence as shown in SEQ ID NO: 12, 14, 16, 18, 20 or 22. Said nucleic acid sequence particularly preferably comprises a sequence as shown in SEQ ID NO: 11, 13, 15, 17, 19 or 21. "Part" means in relation to the nucleic acid sequence preferably a sequence of at least 10 bases, preferably 15 bases, particularly preferably 20 bases, most preferably 30 bases.

Further included according to the invention are methods for identifying and/or isolating promoters of genes which encode a promoter having specificity for nonreproductive floral tissue, wherein at least one nucleic acid sequence or a part thereof is employed in the identification and/or isolation, wherein said nucleic acid sequence encodes an amino acid sequence which comprises at least one sequence as shown in SEQ ID NO: 23, 24, 25, 26, 27, 28, 29, 30, 31 or 32 or a variation indicated for these sequences. Said nucleic acid sequence preferably codes for an amino acid sequence comprising a sequence as shown in SEQ ID NO: 12, 14, 16, 18, 20 or 22. Said nucleic acid sequence particularly preferably comprises a sequence as shown in SEQ ID NO: 11, 13, 15, 17, 19 or 21. "Part" means in relation to the nucleic acid sequence preferably a sequence of at least 10 bases, preferably 15 bases, particularly preferably 20 bases, most preferably 30 bases. In a preferred embodiment, the method of the invention is based on the polymerase chain reaction, wherein said nucleic acid sequence or a part thereof is employed as primer.

Various methods for identifying and isolating the promoter of the corresponding gene, starting from a nucleic acid sequence (e.g. a gene transcript such as, for example, a cDNA) are known to the skilled worker. In principle, all methods for amplifying flanking chromosomal sequences are available for example for this purpose. The two most commonly used methods are inverse PCR ("iPCR"; diagrammatically depicted in FIG. 10) and "Thermal Asymmetric Interlaced PCR" ("TAIL PCR").

For the iPCR, genomic DNA of the organism from which the functionally equivalent promoter is to be isolated is completely digested with a given restriction enzyme, and then the individual fragments are religated, i.e. linked to themselves to give a circular molecule, in a diluted mixture. The large number of resulting circular DNA molecules also includes those comprising the known sequence (for example the sequence coding for the homologous protein). Starting from this, the circular molecule can be amplified by PCR using a primer pair where both primers are able to anneal to the known sequence segment. One possible embodiment of the iPCR is reproduced in example 6.

The TAIL-PCR is based on the use of firstly a set of successively truncated highly specific primers which anneal to the known genomic sequence (for example the sequence coding for the homologous protein), and secondly a set of shorter random primers with a lower melting temperature, so that a less sequence-specific annealing to genomic DNA flanking the known genomic sequence takes place. Annealing of the primers to the DNA to be amplified is possible with such a primer combination making specific amplification of the desired target sequence possible. One possible embodiment of the TAIL-PCR is reproduced for example in example 5.

A further aspect of the invention relates to methods for producing a transgenic expression cassette having specificity for nonreproductive floral tissue, comprising the following steps:

I. isolation of a promoter sequence with specificity for nonreproductive floral tissues, wherein at least one nucleic acid sequence or a part thereof is employed in the isolation, wherein said nucleic acid sequence encodes an amino acid sequence which comprises at least one sequence as shown in SEQ ID NO: 23, 24, 25, 26, 27, 28, 29, 30, 31 or 32 or a variation indicated for these sequences.

II. functional linkage of said promoter with a further nucleic acid sequence, wherein said nucleic acid sequence is heterologous in relation to the promoter.

Said nucleic acid sequence preferably codes for an amino acid sequence comprising a sequence as shown in SEQ ID NO: 12, 14, 16, 18, 20 or 22. Said nucleic acid sequence particularly preferably comprises a sequence as shown in SEQ ID NO: 11, 13, 15, 17, 19 or 21. "Part" means in relation to the nucleic acid sequence preferably a sequence of at least 10 bases, preferably 15 bases, particularly preferably 20 bases, most preferably 30 bases. In a preferred embodiment, the method of the invention is based on the polymerase chain reaction, wherein said nucleic acid sequence or a part thereof is employed as primer. Methods known to the skilled worker, such as, for example, ligation etc., can be employed for the functional linkage (see below).

"Mutation" means substitution, addition, deletion, inversion or insertion of one or more nucleotide residues. Thus, for example, the present invention also comprises nucleotide sequences obtained by modification of the promoters as shown in SEQ ID NO: 1 or 2. The aim of such a modification may be further localization of the sequence comprised therein or, for example, also the insertion of further restriction enzyme cleavage sites, the deletion of excess DNA or the addition of further sequences, for example further regulatory sequences.

Where insertions, deletions or substitutions, such as, for example, transitions and transversions, are appropriate, it is possible to use techniques known per se, such as in vitro mutagenesis, primer repair, restriction or ligation. Transition means a base-pair exchange of a purine/pyrimidine pair into another purine/pyrimidine pair (e.g. A-T for G-C). Transversion means a base-pair exchange of a purine/pyrimidine pair for a pyrimidine/purine pair (e.g. A-T for T-A). Deletion means removal of one or more base pairs. Insertion means introduction of one or more base pairs.

Complementary ends of the fragments for ligation can be made available by manipulations such as, for example, restriction, chewing back or filling in of overhangs for blunt ends. Analogous results are also obtainable by using the polymerase chain reaction (PCR) using specific oligonucleotide primers.

Homology between two nucleic acids means the identity of the nucleic acid sequence over the complete sequence length in each case, which is calculated by comparison with the aid of the GAP program algorithm (Wisconsin Package Version 10.0, University of Wisconsin, Genetics Computer Group (GCG), Madison, USA), setting the following parameters:

Gap Weight: 12 Length Weight: 4
Average Match: 2.912 Average Mismatch:−2.003

For example, a sequence which has a homology of at least 50% based on nuleic acids with the sequence SEQ ID NO: 1 means a sequence which has a homology of at least 50% on comparison with the sequence SEQ ID NO: 1 by the above program algorithm with the above set of parameters.

Homology between two polypeptides means the identity of the amino acid sequence over the respective sequence length, which is calculated by comparison with the aid of the GAP program algorithm (Wisconsin Package Version 10.0, University of Wisconsin, Genetics Computer Group (GCG), Madison, USA), setting the following parameters:

Gap Weight: 8 Length Weight: 2
Average Match: 2.912 Average Mismatch:−2.003

For example, a sequence having a homology of at least 60% based on protein with the sequence SEQ ID NO: 12 means a sequence which has a homology of at least 60% on comparison with the sequence SEQ ID NO: 12 by the above program algorithm with the above set of parameters.

Functional equivalents also means DNA sequences which hybridize under standard conditions with one of the nucleic acid sequences coding for one of the promoters as shown in SEQ ID NO: 1 or 2 or with the nucleic acid sequences complementary thereto, and which have substantially the same promoter properties.

The term standard hybridization conditions is to be understood broadly and means both stringent and less stringent hybridization conditions. Such hybridization conditions are described inter alia in Sambrook J, Fritsch E F, Maniatis T et al., in Molecular Cloning—A Laboratory Manual, 2$^{nd}$ edition, Cold Spring Harbor Laboratory Press, 1989, pages 9.31-9.57 or in Current Protocols in Molecular Biology, John Wiley & Sons, N.Y. (1989), 6.3.1-6.3.6. For example, the conditions during the washing step can be selected from the range of conditions limited by those of low stringency (with approximately 2× SSC at 50° C.) and those of high stringency (with approximately 0.2× SSC at 50° C., preferably at 65° C.) (20× SSC: 0.3 M sodium citrate, 3 M NaCl, pH 7.0). In addition, the temperature during the washing step can be raised from low-stringency conditions at room temperature, approximately 22° C., to more stringent conditions at approximately 65° C. Both parameters, the salt concentration and the temperature, can be varied simultaneously, and it is also possible for one of the two parameters to be kept constant and only the other to be varied. It is also possible to employ denaturing agents such as, for example, formamide or SDS during the hybridization. Hybridization in the presence of 50% formamide is preferably carried out at 42° C. Some exemplary conditions for hybridization and washing step are given below:

(1) Hybridization Conditions with for Example
   a) 4× SSC at 65° C., or
   b) 6× SSC, 0.5% SDS, 100 µg/ml denatured fragmented salmon sperm DNA at 65° C., or
   c) 4× SSC, 50% formamide, at 42° C., or
   d) 2× or 4× SSC at 50° C. (low-stringency condition), or
   e) 2× or 4× SSC, 30 to 40% formamide at 42° C. (low-stringency condition), or
   f) 6× SSC at 45° C., or,
   g) 0.05 M sodium phosphate buffer pH 7.0, 2 mM EDTA, 1% BSA and 7% SDS.

(2) Washing Steps with for Example
   a) 0.1× SSC at 65° C., or
   b) 0.1× SSC, 0.5% SDS at 68° C., or
   c) 0.1× SSC, 0.5% SDS, 50% formamide at 42° C., or
   d) 0.2× SSC, 0.1% SDS at 42° C., or
   e) 2× SSC at 65° C. (low-stringency condition), or
   f) 40 mM sodium phosphate buffer pH 7.0, 1% SDS, 2 mM EDTA.

Methods for preparing functional equivalents of the invention preferably comprise the introduction of mutations into one of the promoters as shown in SEQ ID NO: 1 or 2. Mutagenesis may be random, in which case the mutagenized sequences are subsequently screened for their properties by a trial and error procedure. Particularly advantageous selection criteria comprise for example the level of the resulting expression of the introduced nucleic acid sequence in a nonreproductive floral tissue.

Methods for mutagenesis of nucleic acid sequences are known to the skilled worker and include by way of example the use of oligonucleotides with one or more mutations compared with the region to be mutated (e.g. in a site-specific mutagenesis). Primers with approximately 15 to approximately 75 nucleotides or more are typically employed, with preferably about 10 to about 25 or more nucleotide residues being located on both sides of the sequence to be localized. Details and procedure for said mutagenesis methods are familiar to the skilled worker (Kunkel et al. (1987) Methods Enzymol 154:367-382; Tomic et al. (1990) Nucl Acids Res 12:1656; Upender et al. (1995) Biotechniques 18(1):29-30; U.S. Pat. No. 4,237,224). A mutagenesis can also be achieved by treating for example transgenic expression vectors comprising one of the nucleic acid sequences of the invention with mutagenizing agents such as hydroxylamine.

An alternative possibility is to delete nonessential sequences of a promoter of the invention without significantly impairing the essential properties mentioned. Such deletion variants represent functionally equivalent fragments to the promoters described by SEQ ID NO: 1 or 2 or to functional equivalents thereof. Localization of the promoter sequence to particular essential regulatory regions can be carried out for example with the aid of a search routine to search for promoter elements. Particular promoter elements are often present in increased numbers in the regions relevant for promoter activity. This analysis can be carried out for example with computer programs such as the PLACE program ("Plant Cis-acting Regulatory DNA Elements"; Higo K et al. (1999) Nucl Acids Res 27(1): 297-300), the BIOBASE database "Transfac" (Biologische Datenbanken GmbH, Braunschweig; Wingender E et al. (2001) Nucleic Acids Res 29(1): 281-3) or the PlantCARE database (Lescot M et al. (2002) Nucleic Acids Res 30(1):325-7).

The functionally equivalent fragments of one of the promoters of the invention—for example of the promoters described by SEQ ID NO: 1 or 2—preferably comprise at least 200 base pair, very particularly preferably at least 500 base pairs, most preferably at least 1000 base pairs of the 3' end of the respective promoter of the invention—for example of the promoters described by SEQ ID NO: 1 or 2—the length being calculated from the translation start ("ATG" codon) upstream in the 5' direction. Very especially preferred functionally equivalent fragments are the promoter sequences described by SEQ ID NO: 3 or 4. Further functionally equivalent fragments may be generated for example by deleting any 5'-untranslated regions still present. For this purpose, the start of transcription of the corresponding genes can be determined by methods familiar to the skilled worker (such as, for example, 5'-RACE), and the 5'-untranslated regions can be deleted by PCR-mediated methods or endonuclease digestion.

In transgenic expression cassettes of the invention, at least one of the promoters of the invention (e.g. described by SEQ ID NO: 1, 2, 3 or 4) is functionally linked to at least one nucleic acid sequence to be expressed transgenically.

A functional linkage means, for example, the sequential arrangement of one of the promoters of the invention (e.g. described by SEQ ID NO: 1, 2, 3 or 4) with a nucleic acid sequence to be expressed transgenically and, where appropriate, further genetic control sequences such as, for example, a terminator or a polyadenylation sequence in such a way that the promoter is able to fulfill its function in the transgenic expression of the nucleic acid sequence under suitable conditions, and expression of the nucleic acid sequence (i.e. transcription and, where appropriate, translation) takes place. "Suitable conditions" means in this connection preferably the presence of the expression cassette in a plant cell, preferably a plant cell comprised in a nonreproductive floral tissue of a plant.

Arrangements in which the nucleic acid sequence to be expressed transgenically is positioned behind one of the promoters of the invention (e.g. described by SEQ ID NO: 1, 2, 3 or 4), so that the two sequences are covalently connected together, are preferred. In this connection, the distance between the promoter sequence and the nucleic acid sequence to be expressed transgenically is preferably less than 200 base pairs, particularly preferably less than 100 base pairs, very particularly preferably less than 50 base pairs.

Production of a functional linkage and production of a transgenic expression construct can be achieved by means of conventional recombination and cloning techniques as described for example in Maniatis T, Fritsch E F and Sambrook J (1989) Molecular Cloning: A Laboratory Manual, Cold Spring Harbor Laboratory, Cold Spring Harbor (NY), in Silhavy T J, Berman M L and Enquist L W (1984) Experiments with Gene Fusions, Cold Spring Harbor Laboratory, Cold Spring Harbor (NY) and in Ausubel F M et al. (1987) Current Protocols in Molecular Biology, Greene Publishing Assoc. and Wiley Interscience. However, further sequences which have for example the function of a linker with particular restriction enzyme cleavage sites or of a signal peptide may also be positioned between the two sequences. Insertion of sequences may also lead to expression of fusion proteins. It is possible and preferred for the transgenic expression construct, consisting of a linkage of promoter and nucleic acid sequence to be expressed, to be integrated into a vector and be inserted into a plant genome for example by transformation.

However, an expression cassette also means constructions in which one of the promoters of the invention (e.g. described by SEQ ID NO: 1, 2, 3 or 4) was, without necessarily having been functionally linked beforehand to a nucleic acid sequence to be expressed, introduced into a host genome, for example by targeted homologous recombination or random insertion, there undertakes regulatory control over endogenous nucleic acid sequences then functionally linked thereto, and controls the transgenic expression thereof. Insertion of the promoter—for example by a homologous recombination—in front of a nucleic acid coding for a particular polypeptide results in an expression cassette of the invention which controls the expression of the particular polypeptide selectively in the nonreproductive floral tissues. It is also possible for example for the natural promoter of an endogenous gene to be replaced by one of the promoters of the invention (e.g. described by SEQ ID NO: 1, 2, 3 or 4), and for the expression behavior of the endogenous gene to be modified.

A further possibility is also for the promoter to be inserted in such a way that antisense RNA to the nucleic acid coding for a particular polypeptide is expressed. In this way, expression of the particular polypeptide in the nonreproductive organs of the flower is selectively downregulated or switched off.

It is also possible analogously for a nucleic acid sequence which is to be expressed transgenically to be placed—for example by homologous recombination—behind the sequence which codes for one of the promoters of the invention (e.g. described by SEQ ID NO: 1, 2, 3 or 4), and which is located in its natural chromosomal context, so as to result in an expression cassette of the invention which controls the expression of the nucleic acid sequence to be expressed transgenically in the nonreproductive floral tissues.

The transgenic expression cassettes of the invention may comprise further genetic control sequences. The term genetic control sequences is to be understood broadly and means all sequences having an influence on the coming into existence or the function of a transgenic expression cassette of the invention. Genetic control sequences modify for example the transcription and translation in prokaryotic or eukaryotic organisms. The transgenic expression cassettes of the invention preferably comprise as additional genetic control sequence a terminator sequence 3' downstream from the particular nucleic acid sequence to be expressed transgenically, and where appropriate further customary regulatory elements, in each case functionally linked to the nucleic acid sequence to be expressed transgenically.

Genetic control sequences also comprise further promoters, promoter elements or minimal promoters able to modify the expression-controlling properties. It is thus possible for example through genetic control sequences for tissue-specific expression to take place additionally in dependence on particular stress factors. Corresponding elements are described for example for water stress, abscisic acid (Lam E and Chua N H, J Biol Chem 1991; 266(26): 17131-17135) and heat stress (Schoffl F et al. (1989) Mol Gen Genetics 217(2-3): 246-53).

A further possibility is for further promoters which make transgenic expression possible in further plant tissues or in other organisms such as, for example, *E. coli* bacteria to be functionally linked to the nucleic acid sequence to be expressed. Suitable promoters are in principle all plant-specific promoters. Plant-specific promoters means in principle every promoter able to control the expression of genes, in particular foreign genes, in plants or plant parts, cells, tissues, cultures. It is moreover possible for expression to be for example constitutive, inducible or development-dependent. Preference is given to constitutive promoters, tissue-specific promoters, development-dependent promoters, chemically inducible, stress-inducible or pathogen-inducible promoters. Corresponding promoters are generally known to the skilled worker.

Further advantageous control sequences are to be found for example in the promoters of gram-positive bacteria such as amy and SPO2 or in the yeast or fungal promoters ADC1, MFa, AC, P-60, CYC1, GAPDH, TEF, rp28, ADH.

It is possible in principle for all natural promoters with their regulatory sequences like those mentioned above to be used for the method of the invention. It is additionally also possible for synthetic promoters to be used advantageously.

Genetic control sequences further comprise also the 5'-untranslated regions, introns or noncoding 3'-region of genes such as, for example, the actin-1 intron, or the Adh1-S introns 1, 2 and 6 (generally: The Maize Handbook, Chapter 116, Freeling and Walbot, Eds., Springer, N.Y. (1994)), preferably the genes with the gene locus At3g01980 and At1g63140 from Arabidopsis thaliana. It is possible to show that such regions may have a significant function in regulating gene expression. Thus, it has been shown that 5'-untranslated sequences are able to enhance the transient expression of heterologous genes. Examples of translation enhancers which may be mentioned are the 5' leader sequence from the tobacco mosaic virus (Gallie et al. (1987) Nucl Acids Res 15:8693-8711) and the like. They may in addition promote tissue specificity (Rouster J et al. (1998) Plant J 15:435-440). The nucleic acid sequences indicated in SEQ ID NO: 1, 2, 3 or 4 in each case represent the promoter region and the 5'-untranslated regions up to before the ATG start codon of the respective genes with the gene locus At3g01980 and At1g63140.

The transgenic expression construct may advantageously comprise one or more so-called enhancer sequences functionally linked to the promoter, which make increased transgenic expression of the nucleic acid sequence possible. Additional advantageous sequences can also be inserted at the 3' end of the nucleic acid sequences to be expressed transgenically, such as further regulatory elements or terminators. The nucleic acid sequences to be expressed transgenically may be comprised in one or more copies in the gene construct.

Polyadenylation signals suitable as control sequences are plant polyadenylation signals, preferably those which are essentially T-DNA polyadenylation signals from *Agrobacterium tumefaciens*. Examples of particularly suitable terminator sequences are the OCS (octopine synthase) terminator and the NOS (nopaline synthase) terminator.

Control sequences additionally mean those which make homologous recombination or insertion into the genome of a host organism possible or allow deletion from the genome. In homologous recombination for example the coding sequence of a particular endogenous gene can be specifically replaced by a sequence coding for a dsRNA. Methods such as cre/lox technology permit tissue-specific, and in some circumstances inducible, deletion of the transgenic expression construct from the genome of the host organism (Sauer B (1998) Methods 14(4):381-92). In this case, particular flanking sequences are attached to the target gene (lox sequences) and make later deletion by means of cre recombinase possible.

A transgenic expression cassette and/or the transgenic expression vectors derived therefrom may comprise further functional elements. The term functional element is to be understood broadly and means all elements which have an influence on the production, replication or function of the transgenic expression constructs of the invention, of the transgenic expression vectors or of the transgenic organisms. Non-restrictive examples which may be mentioned are:

a) Selection markers which confer resistance to biocides such as metabolism inhibitors (e.g. 2-deoxyglucose 6-phosphate;

WO 98/45456), antibiotics (e.g. kanamycin, G 418, bleomycin, hygromycin) or—preferably—herbicides (e.g. phosphinothricin). Examples of selection markers which may be mentioned are: phosphinothricin acetyltransferases (bar and pat gene), which inactivate glutamine synthase inhibitors, 5-enolpyruvylshikimate-3-phosphate synthases (EPSP synthase genes) which confer resistance to glyphosate (N-(phosphonomethyl)glycine), glyphosate-degrading enzymes (gox gene product; glyphosate oxidoreductase), dehalogenases which for example inactivate dalapon (deh gene product), sulfonylurea- and imidazolinone-inactivating acetolactate synthases, and nitrilases which for example degrade bromoxynil (bxn gene product), the aasa gene product which confers resistance to the antibiotic apectinomycin, streptomycin phosphotransferases (SPT) which ensure resistance to streptomycin, neomycin phosphotransferases (NPTII) which confer resistance to kanamycin or geneticidin, the hygromycin phosphotransferases (HPT) which mediate resistance to hygromycin, the acetolactate synthases (ALS) which confer resistance to sulfonylurea herbicides (e.g. mutated ALS variants with, for example, the S4 and/or Hra mutation).

b) Reporter genes which code for easily quantifiable proteins and ensure via an intrinsic color or enzymic activity an assessment of the transformation efficiency or of the location or timing of the expression. Very particular preference is given in this connection to reporter proteins (Schenborn E, Groskreutz D. Mol Biotechnol. 1999; 13(1): 29-44) such as the green fluorescence protein (GFP) (Sheen et al. (1995) Plant Journal 8(5):777-784), the chloramphenicol transferase, a luciferase (Ow et al. (1986) Science 234:856-859), the aequorin gene (Prasher et al. (1985) Biochem Biophys Res Commun 126(3):1259-1268), the β-galactosidase, with very particular preference for β-glucuronidase (Jefferson et al. (1987) EMBO J 6:3901-3907).

c) Origins of replication which ensure replication of the transgenic expression constructs or transgenic expression vectors of the invention in, for example, E. coli. Examples which may be mentioned are ORI (origin of DNA replication), the pBR322 ori or the P15A ori (Sambrook et al.: Molecular Cloning. A Laboratory Manual, $2^{nd}$ ed. Cold Spring Harbor Laboratory Press, Cold Spring Harbor, N.Y., 1989).

d) Elements which are necessary for *agrobacterium*-mediated plant transformation, such as, for example, the right or left border of the T-DNA or the vir region.

"Introduction" comprises for the purposes of the invention all methods suitable for introducing a nucleic acid sequence (for example an expression cassette of the invention) directly or indirectly into an organism (e.g. a plant) or a cell, compartment, tissue, organ or propagation material (e.g. seeds or fruits) thereof, or for generating such therein. Direct and indirect methods are comprised. The introduction can lead to a temporary (transient) presence of said nucleic acid sequence or else to a permanent (stable) presence. Introduction comprises for example methods such as transfection, transduction or transformation. The organisms used in the methods are grown or cultured, depending on the host organism, in the manner known to the skilled worker.

Introduction of a transgenic expression cassette of the invention into an organism or cells, tissues, organs, parts or seeds thereof (preferably into plants or plant cells, tissues, organs, parts or seeds) can advantageously be achieved by use of vectors comprising the transgenic expression cassettes. Vectors may be for example plasmids, cosmids, phages, viruses or else *agrobacteria*. The transgenic expression cassettes can be inserted into the vector (preferably a plasmid vector) via a suitable restriction cleavage site. The resulting vector can be firstly introduced and amplified in E. coli. Correctly transformed E. coli are selected and cultured, and the recombinant vector is isolated by methods familiar to the skilled worker. Restriction analysis and sequencing can be used to check the cloning step.

Preferred vectors are those making stable integration of the expression cassette into the host genome possible. Production of a transformed organism (or of a transformed cell or tissue) requires introduction of the appropriate DNA (e.g. the expression vector) or RNA into the appropriate host cell. A large number of methods is available for this process, which is referred to as transformation (or transduction or transfection) (Keown et al. (1990) Methods in Enzymology 185:527-537). Thus, the DNA or RNA can for example be introduced directly by microinjection or by bombardment with DNA-coated microparticles. The cell can also be permeabilized chemically, for example with polyethylene glycol, so that the DNA is able to enter the cell by diffusion. The DNA introduction can also take place by protoplast fusion with other DNA-comprising units such as minicells, cells, lysosomes or liposomes. Electroporation is another suitable method for introducing DNA, in which the cells are reversibly permeabilized by an electrical impulse. Corresponding methods are described (for example in Bilang et al. (1991) Gene 100:247-250; Scheid et al. (1991) Mol Gen Genet 228:104-112; Guerche et al. (1987) Plant Science 52:111-116; Neuhause et al. (1987) Theor Appl Genet 75:30-36; Klein et al. (1987) Nature 327:70-73; Howell et al. (1980) Science 208:1265; Horsch et al. (1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

Vectors preferred for expression in E. coli are pQE70, pQE60 and pQE-9 (QIAGEN, Inc.); pBluescript vectors, Phagescript vectors, pNH8A, pNH16a, pNH18A, pNH46A (Stratagene Cloning Systems, Inc.); ptrc99a, pKK223-3, pKK233-3, pDR540, pRIT5 (Pharmacia Biotech, Inc.).

Preferred vectors for expression in mammalian cells comprise pWLNE0, pSV2CAT, pOG44, pXT1 and pSG (Stratagene Inc.); pSVK3, pBPV, pMSG and pSVL (Pharmacia Biotech, Inc.). Inducible vectors which may be mentioned are pTet-tTak, pTet-Splice, pcDNA4/TO, pcDNA4/TO /LacZ, pcDNA6/TR, pcDNA4/TO/Myc-His/LacZ, pcDNA4/TO/Myc-His A, pcDNA4/TO/Myc-His B, pcDNA4/TO/Myc-His C, pVgRXR (Invitrogen, Inc.) or the pMAM series (Clontech, Inc.; GenBank Accession No: U02443). These themselves provide the inducible regulatory control element for example for a chemically inducible expression.

Vectors for expression in yeast comprise for example pYES2, pYD1, pTEF1/Zeo, pYES2/GS, pPICZ, pGAPZ, pGAPZalph, pPIC9, pPIC3.5, PHIL-D2, PHIL-S1, pPIC3SK, pPIC9K, and PA0815 (Invitrogen, Inc.).

Cloning vectors and techniques for genetic manipulation of ciliates and algae are known to the skilled worker (WO 98/01572; Falciatore et al. (1999) Marine Biotechnology 1(3):239-251; Dunahay et al. (1995) J Phycol 31:10004-1012).

The methods to be used in principle for the transformation of animal cells or of yeast cells are similar to those for "direct" transformation of plant cells. Methods such as calcium phosphate or liposome-mediated transformation or else electroporation are preferred in particular.

Various methods and vectors for inserting genes into the genome of plants and for regenerating plants from plant tissues or plant cells are known (Plant Molecular Biology and Biotechnology (CRC Press, Boca Raton, Fla.), Chapter 6/7, pp. 71-119 (1993); White F F (1993) Vectors for Gene Transfer in Higher Plants; in: Transgenic Plants, Vol. 1, Engineering and Utilization, editors: Kung and Wu R, Academic Press, 15-38; Jenes B et al. (1993) Techniques for Gene Transfer, in: Transgenic Plants, Vol. 1, Engineering and Utilization, editors: Kung and R. Wu, Academic Press, pp. 128-143; Potrykus (1991) Annu Rev Plant Physiol Plant Molec Biol 42:205-225; Halford N G, Shewry P R (2000) Br Med Bull 56(1):62-73). Those mentioned above are included, for example. In the case of plants, the described methods for the transformation and regeneration of plants from plant tissues or plant cells are used for transient or stable transformation. Suitable methods are, in particular, protoplast transformation by polyethylene glycol-induced DNA uptake, calcium phosphate-mediated transformation, DEAE-dextran-mediated transformation, liposome-mediated transformation (Freeman et al. (1984) Plant Cell Physiol. 29:1353ff; U.S. Pat. No. 4,536,475), biolistic methods with the gene gun ("particle bombardment" method; U.S. Pat. No. 5,100,792; EP-A 0 444 882; EP-A 0 434 616; Fromm M E et al. (1990) Bio/Technology 8(9):833-9; Gordon-Kamm et al. (1990) Plant Cell 2:603), electroporation, incubation of dry embryos in DNA-containing solution, electroporation (EP-A 290 395, WO 87/06614), microinjection (WO 92/09696, WO 94/00583, EP-A 0 331 083, EP-A 0 175 966) or other methods of direct DNA introduction (DE 4 005 152, WO 90/12096, U.S. Pat. No. 4,684,611). Physical methods of DNA introduction into plant cells are surveyed in Oard (1991) Biotech Adv 9:1-11.

In the case of these "direct" transformation methods, no particular requirements need be met by the plasmid used. Simple plasmids such as those of the pUC series, pBR322, M13mp series, pACYC184 etc. can be used. If complete plants are to be regenerated from the transformed cells, it is necessary for an additional selectable marker gene to be present on the plasmid.

Besides these "direct" transformation techniques, it is also possible to carry out a transformation by bacterial infection using *agrobacterium* (e.g. EP 0 116 718), viral infection using viral vectors (EP 0 067 553; U.S. Pat. No. 4,407,956; WO 95/34668; WO 93/03161) or using pollen (EP 0 270 356; WO 85/01856; U.S. Pat. No. 4,684,611).

The transformation is preferably effected using *agrobacteria* which comprise disarmed Ti plasmid vectors, utilizing their natural ability to transfer genes to plants (EP-A 0 270 355; EP-A 0 116 718).

*Agrobacterium* transformation is widely used for the transformation of dicotyledons, but is also increasingly being applied to monocotyledons (Toriyama et al. (1988) Bio/Technology 6: 1072-1074; Zhang et al. (1988) Plant Cell Rep 7:379-384; Zhang et al. (1988) Theor Appl Genet 76:835-840; Shimamoto et al. (1989) Nature 338:274-276; Datta et al. (1990) Bio/Technology 8: 736-740; Christou et al. (1991) Bio/Technology 9:957-962; Peng et al. (1991) International Rice Research Institute, Manila, Philippines 563-574; Cao et al. (1992) Plant Cell Rep 11:585-591; Li et al. (1993) Plant Cell Rep 12:250-255; Rathore et al. (1993) Plant Mol Biol 21:871-884; Fromm et al. (1990) Bio/Technology 8:833-839; Gordon-Kamm et al. (1990) Plant Cell 2:603-618; D'Halluin et al. (1992) Plant Cell 4:1495-1505; Walters et al. (1992) Plant Mol Biol 18:189-200; Koziel et al. (1993) Biotechnology 11:194-200; Vasil I K (1994) Plant Mol Biol 25:925-937; Weeks et al. (1993) Plant Physiol 102:1077-1084; Somers et al. (1992) Bio/Technology 10:1589-1594; WO 92/14828; Hiei et al. (1994) Plant J 6:271-282).

The strains mostly used for *agrobacterium* transformation, *Agrobacterium tumefaciens* or *Agrobacterium rhizogenes* comprise a plasmid (Ti or Ri plasmid) which is transferred to the plant after *agrobacterium* infection. Part of this plasmid, called T-DNA (transferred DNA), is integrated into the genome of the plant cell. Alternatively, binary vectors (mini-Ti plasmids) can also be transferred into plants and integrated in the genome thereof by *agrobacterium*.

The use of *Agrobacterium tumefaciens* for the transformation of plants using tissue culture explants is described (inter alia Horsch R B et al. (1985) Science 225:1229ff.; Fraley et al. (1983) Proc Natl Acad Sci USA 80: 4803-4807; Bevans et al. (1983) Nature 304:184-187). Many *Agrobacterium tumefaciens* strains are able to transfer genetic material—for example the expression cassettes of the invention—such as, for example, the strains EHA101[pEHA101], EHA105 [pEHA105], LBA4404[pAL4404], C58C1[pMP90] and C58C1[pGV2260] (Hood et al. (1993) Transgenic Res 2:208-218; Hoekema et al. (1983) Nature 303:179-181; Koncz and Schell (1986) Gen Genet 204:383-396; Deblaere et al. (1985) Nucl Acids Res 13: 4777-4788).

On use of *agrobacteria*, the expression cassette must be integrated into specific plasmids either into a shuttle, or intermediate, vector or into a binary vector. Binary vectors, which are able to replicate both in *E. coli* and in *agrobacterium*, are preferably used. They normally comprise a selection marker gene and a linker or polylinker, flanked by the right and left T-DNA border sequence. They can be transformed directly into *agrobacterium* (Holsters et al. (1978) Mol Gen Genet 163:181-187). The *agrobacterium* acting as host organism in this case should already comprise a plasmid having the vir region. This is necessary for transfer of the T-DNA into the plant cell. An *agrobacterium* transformed in this way can be used to transform plant cells. The use of T-DNA for transforming plant cells has been intensively investigated and described (EP-A 0 120 516; Hoekema, In: The Binary Plant Vector System, Offsetdrukkerij Kanters B. V., Alblasserdam, Chapter V; An et al. (1985) EMBO J 4:277-287). Various binary vectors are known, and some of them are commercially available, such as, for example, pBI101.2 or pBIN19 (Clontech Laboratories, Inc. USA; Bevan et al. (1984) Nucl Acids Res 12:8711), pBinAR, pPZP200 or pPTV.

*Agrobacteria* transformed with such a vector can then be used in a known manner for transforming plants, especially crop plants such as, for example, oilseed rape, by for example bathing wounded leaves or pieces of leaf in a solution of *agrobacteria* and then cultivating in suitable media. Transformation of plants by *agrobacteria* is described (White F F (1993) Vectors for Gene Transfer in Higher Plants; in Transgenic Plants, Vol. 1, Engineering and Utilization, edited by SD Kung and R Wu, Academic Press, pp. 15-38; Jenes B et al. (1993) Techniques for Gene Transfer, in: Transgenic Plants, Vol. 1, Engineering and Utilization, edited by S. D. Kung and R. Wu, Academic Press, pp. 128-143; Potrykus (1991) Annu Rev Plant Physiol Plant Molec Biol 42:205-225). Transgenic plants which have integrated the expression systems of the invention described above can be regenerated in a known manner from the transformed cells of the wounded leaves or pieces of leaf.

Stably transformed cells (i.e. those which have integrated the introduced DNA into the DNA of the host cell) can be selected from untransformed ones if a selectable marker is a constituent of the introduced DNA. Any gene able to confer a resistance (see above) to a biocide (e.g. an antibiotic or herbicide, see above) can act as marker, for example. Transformed cells which express such a marker gene are able to survive in the presence of concentrations of a corresponding biocide which kill an untransformed wild type. The selection marker permits the selection of transformed cells from untransformed ones (McCormick et al. (1986) Plant Cell Reports 5:81-84). The resulting plants can be grown and crossed in the usual way. Two or more generations should be cultivated in order to ensure that the genomic integration is stable and heritable.

As soon as a transformed plant cell has been produced, it is possible to obtain a complete plant by using methods known to the skilled worker. These entail, for example, starting from callus cultures, single cells (e.g. protoplasts) or leaf disks (Vasil et al. (1984) Cell Culture and Somatic Cell Genetics of Plants, Vol I, II and III, Laboratory Procedures and Their Applications, Academic Press; Weissbach and Weissbach (1989) Methods for Plant Molecular Biology, Academic Press). The formation of shoot and root from these still undifferentiated callus cell masses can be induced in a known manner. The resulting shoots can be planted out and grown. Corresponding methods are described (Fennell et al. (1992) Plant Cell Rep. 11: 567-570; Stoeger et al (1995) Plant Cell Rep. 14:273-278; Jahne et al. (1994) Theor Appl Genet 89:525-533).

The effectiveness of expression of the transgenically expressed nucleic acids can be estimated for example in vitro by shoot-meristem propagation using one of the selection methods described above. In addition, a change in the type and level of expression of a target gene, and the effect on the phenotype of the plant can be tested on test plants in glasshouse tests.

A further aspect of the invention relates to transgenic organisms transformed with at least one expression cassette of the invention or one vector of the invention, and cells, cell cultures, tissues, parts—such as, for example, in the case of plant organisms leaves, roots etc.—or propagation material derived from such organisms.

By organism, starting or host organisms are meant prokaryotic or eukaryotic organisms such as, for example, microorganisms or plant organisms. Preferred microorganisms are bacteria, yeasts, algae or fungi.

Preferred bacteria are bacteria of the genus *Escherichia, Erwinia, Agrobacterium, Flavobacterium, Alcaligenes, Pseudomonas, Bacillus* or cyanobacteria, for example of the genus *Synechocystis* and further bacterial genera described in Brock Biology of Microorganisms Eighth Edition on pages A-8, A-9, A10 and A11.

Microorganisms which are particularly preferred are those able to infect plants and thus transfer the constructs of the invention. Preferred microorganisms are those of the genus *Agrobacterium* and especially of the species *Agrobacterium tumefaciens*. Particularly preferred microorganisms are those able to produce toxins (e.g. botulinus toxin), pigments (e.g. carotenoids or flavonoids), antibiotics (e.g. penicillin), phenylpropanoids (e.g. tocopherol), polyunsaturated fatty acids (e.g. arachidonic acid) or vitamins (e.g. vitamin B12).

Preferred yeasts are *Candida, Saccharomyces, Hansenula* or *Pichia*.

Preferred fungi are *Aspergillus, Trichoderma, Ashbya, Neurospora, Fusarium, Beauveria* or further fungi described in Indian Chem Engr. Section B. Vol 37, No. 1,2 (1995) on page 15, table 6.

Host or starting organisms preferred as transgenic organisms are in particular plant organisms.

"Plant organism or cells derived therefrom" means in general every cell, tissue, part or propagation material (such as seeds or fruits) of an organism capable of photosynthesis. Included for the purposes of the invention are all genera and species of higher and lower plants of the plant kingdom. Annual, perennial, monocotyledonous and dicotyledonous plants are preferred.

"Plant" means for the purposes of the invention all genera and species of higher and lower plants of the plant kingdom. The term includes the mature plants, seeds, shoots and seedlings, and parts derived therefrom, propagation material (for example tubers, seeds or fruits), plant organs, tissues, protoplasts, callus and other cultures, for example cell or callus cultures, and all other types of groupings of plant cells to functional or structural units. Mature plants means plants at any stage of development beyond seedling. Seedling means a young, immature plant at an early stage of development.

Plant organisms for the purposes of the invention are additionally further photosynthetically active organisms such as, for example, algae, cyanobacteria and mosses. Preferred algae are green algae, such as, for example, algae of the genus *Haematococcus, Phaedactylum tricornatum, Volvox* or *Dunaliella. Synechocystis, Chlamydomonas* and *Scenedesmus* are particularly preferred.

Particularly preferred for the purposes of the method of the invention are plant organisms selected from the group of flowering plants (Phylum Anthophyta "angiosperms"). All annual and perennial, monocotyledonous and dicotyledonous plants are comprised. The plant is preferably selected from the following plant families: Amaranthaceae, Asteraceae, Brassicaceae, Caryophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae and Umbelliferae.

The invention is very particularly preferably applied to dicotyledonous plant organisms. Preferred dicotyledonous plants are in particular selected from the dicotyledonous crop plants such as, for example the following 1) Category: Dicotyledonae (dicotyledons). Preferred families:
Aceraceae (maples)
Cactaceae (cacti)
Rosaceae (roses, apples, almonds, strawberries)
Salicaceae (willows)
Asteraceae (compositae) especially the genus *Lactuca*, very especially the species *sativa* (lettuce), and sunflower, dandelion, *Tagetes* or *Calendula* and many others,
Cruciferae (Brassicaceae), especially the genus *Brassica*, very especially the species *napus* (oilseed rape), *campestris* (beet), *oleracea* (e.g. cabbage, cauliflower or broccoli and other *brassica* species); and of the genus *Arabidopsis*, very especially the species *thaliana*, and cress, radish, canola and many others,
Cucurbitaceae such as melon, pumpkin squash, cucumber or zucchini and many others,
Leguminosae (Fabaceae) especially the genus *Glycine*, very especially the species *max* (soybean), soya and alfalfa, pea, beans, lupin or peanut and many others,
Malvaceae, especially mallow, cotton, edible marshmallow, hibiscus and many others,
Rubiaceae, preferably of the subclass Lamiidae such as, for example, *Coffea arabica* or *Coffea liberica* (coffee bush) and many others,
Solanaceae, especially the genus *Lycopersicon*, very especially the species *esculentum* (tomato) and the genus *Solanum*, very especially the species *tuberosum* (potato) and *melongena* (eggplant) and the genus *Capsicum*, very especially the species. *annuum* (paprika), and tobacco, petunia and many others,
Sterculiaceae, preferably of the subclass Dilleniidae such as, for example, *Theobroma cacao* (cocoa bush) and many others,
Theaceae, preferably of the subclass Dilleniidae such as, for example, *Camellia sinensis* or *Thea sinensis* (tea bush) and many others,
Umbelliferae (Apiaceae), especially the genus *Daucus* (very especially the species *carota* (carrot), *Apium* (very especially the species *graveolens dulce* (celeriac)), and parsley and many others; and *linum*, hemp, flax, spinach, carrot, sugarbeet and the various tree, nut and vine species, especially banana and kiwi fruit.

However, in addition, monocotyledonous plants are also suitable. These are preferably selected from the monocotyledonous crop plants such as, for example the families
Arecaceae (palms)
Bromeliaceae (pineapple, spanish moss)
Cyperaceae (sedges)
Liliaceae (lilies, tulips, hyacinths, onions, garlic)
Orchidaceae (orchids)
Poaceae (grasses, bamboos, corn, sugarcane, wheat)
Iridaceae (buckwheat, gladioli, crocuses)
Very particular preference is given to Gramineae such as rice, corn, wheat or other cereal species such as barley, sorghum and millet, rye, triticale or oats, and the sugarcane, and all species of grasses.

Within the framework of the expression cassette of the invention, expression of a particular nucleic acid may, through a promoter having specificity for the nonreproductive organs of the flower, lead to the formation of sense RNA, antisense RNA or double-stranded RNA in the form of an inverted repeat (dsRNAi). The sense RNA can subsequently be translated into particular polypeptides. It is possible with the antisense RNA and dsRNAi to down regulate the expression of particular genes.

The method of gene regulation by means of double-stranded RNA ("double-stranded RNA interference"; dsRNAi) has been described in animal and plant organisms many times (e.g. Matzke M A et al. (2000) Plant Mol Biol 43:401-415; Fire A et al (1998) Nature 391:806-811; Wo 99/32619; WO 99/53050; WO 00/68374; WO 00/44914; WO 00/44895; WO 00/49035; WO 00/63364). Express reference is made to the processes and methods described in the citations indicated.

The specificity of the expression constructs and vectors of the invention for flowers of plants is particularly advantageous. The flower has a function in attracting beneficial insects through incorporation of pigments or synthesis of volatile chemicals.

The natural defense mechanisms of the plant, for example against pathogens, are often inadequate. Introduction of foreign genes from plants, animals or microbial sources may enhance the defenses. Examples are protection against insect damage to tobacco through expression of the *Bacillus thuringiensis* endotoxin (Vaeck et al. (1987) Nature 328:33-37) or protection of tobacco from fungal attack through expression of a chitinase from beans (Broglie et al. (1991) Science 254: 1194-1197).

Cold spells during the flowering period lead to considerable crop losses every year. Targeted expression of protective proteins specifically in the flowering period may provide protection.

For such genetic engineering approaches to be highly efficient it is advantageous for there to be concentrated expression of the appropriate nucleic acid sequence to be expressed transgenically in particular in the petals of the flower. Constitutive expression in the whole plant may make the effect problematic, for example through dilution, or impair the growth of the plant or the quality of the plant product. In addition, there may through constitutive expression be increased switching-off of the transgene ("gene silencing").

Promoters having specificity for the flower are advantageous in this connection. The skilled worker is aware of a large number of proteins whose recombinant expression in the flower is advantageous. The skilled worker is also aware of a large number of genes through which advantageous effects can likewise be achieved through repression or switching-off thereof by means of expression of a corresponding antisense RNA. Non-restrictive examples of advantageous effects which may be mentioned are: achieving resistance to abiotic stress factors (heat, cold, drought, increased moisture, environmental toxins, UV radiation) and biotic stress factors (pathogens, viruses, insects and diseases), improving the properties of human and animal foods, improving the growth rate or the yield, achieving a longer or earlier flowering period, altering or enhancing the scent or the coloring of the flowers. Non-restrictive examples of the nucleic acid sequences or polypeptides which can be employed in these applications and which may be mentioned are:

1. Improved UV protection of the flowers of plants through alteration of the pigmentation through expression of particular polypeptides such as enzymes or regulators of flavonoid biosynthesis (e.g. chalcone synthases, phenylalanine ammonia-lyases), of DNA repair (e.g. photolyases; Sakamoto A et al. (1998) DNA Seq 9(5-6):335-40), of isoprenoid biosynthesis (e.g. deoxyxylulose-5-phosphate synthases), of IPP synthesis or of carotenoid biosynthesis (e.g. phytoene synthases, phytoene desaturases, lycopene cyclases, hydroxylases or ketolases). Preference is given to nucleic acids which code for the *Arabidopsis thaliana* chalcone synthase (GenBank Acc. No.: M20308), the *Arabidopsis thaliana* 6-4 photolyase (GenBank Acc. No.:

BAB00748) or the *Arabidopsis thaliana* blue light photoreceptor/photolyase homolog (PHH1) (GenBank Acc. No.: U62549) or functional equivalents thereof.

2. Improved protection of the flower of plants from abiotic stress factors such as drought, heat or cold, for example through overexpression of the antifreeze polypeptides (e.g. from *Myoxocephalus scorpius*; WO 00/00512), of the *Arabidopsis thaliana* transcription activator CBF1, glutamate dehydrogenases (WO 97/12983, WO 98/11240), of a late embryogenesis gene (LEA), for example from barley (WO 97/13843), calcium-dependent protein kinase genes (WO 98/26045), calcineurins (WO 99/05902), farnesyl transferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechnology and Genetic Engeenering Reviews 15:1-32), DREB1A factor (dehydration response element B 1A; Kasuga M et al. (1999) Nature Biotechnology 17:276-286), genes of mannitol or trehalose synthesis (e.g. trehalose-phosphate synthases; trehalose-phosphate phosphatases, WO 97/42326); or through inhibition of genes such as of trehalase (WO 97/50561). Particular preference is given to nucleic acids which code for the *Arabidopsis thaliana* transcriptional activator CBF1 (Gen-Bank Acc. No.: U77378) or the antifreeze protein from Myoxocephalus octodecemspinosus (Gen-Bank Acc. No.: AF306348) or functional equivalents thereof.

3. Achieving resistance for example to fungi, insects, nematodes and diseases through targeted secretion or accumulation of certain metabolites or proteins in the flower. Examples which may be mentioned are glucosinolates (nematode defense), chitinases or glucanases and other enzymes which destroy the cell wall of parasites, ribosome-inactivating proteins (RIPs) and other proteins of the plant resistance and stress response, like those induced on injury or microbial attack of plants or chemically by, for example, salicylic acid, jasmonic acid or ethylene, lysozymes from non-plant sources such as, for example, T4 lysozyme or lysozme from various mammals, insecticidal proteins such as *Bacillus thuringiensis* endotoxin, α-amylase inhibitor or protease inhibitors (cowpea trypsin inhibitor), glucanases, lectins (e.g. phytohemagglutinin, snowdrop lectin, wheatgerm agglutinin), RNAses or ribozymes. Particular preference is given to nucleic acids which code for the chit42 endochitinase from *Trichoderma harzianum* (GenBank Acc. No.: S78423) or for the N-hydroxylating, multifunctional cytochrome P-450 (CYP79) from *Sorghum bicolor* (GenBank Acc. No.: U32624) or functional equivalents thereof.

4. Achieving defense against or attraction of insects, for example through increased release of volatile scents or messengers through, for example, enzymes of terpene biosynthesis.

5. Achieving an ability to store in flower tissues which normally comprise no storage proteins or lipids, with the aim of increasing the yield of these substances, e.g. by expression of an acetyl-CoA carboxylase or of enzymes for esterification of metabolites. Preference is given to nucleic acids which code for the *Medicago sativa* acetyl-CoA carboxylase (Accase) (GenBank Acc. No.: L25042) or functional equivalents thereof.

6. Expression of transport proteins which improve the uptake of metabolites, nutrients or water into the flower and thus optimize flower growth, metabolite composition or yield, for example through expression of an amino acid transporter which increases the rate of uptake of amino acids, or of a monosaccharide transporter which promotes the uptake of sugars. Preference is given to nucleic acids which code for the *Arabidopsis thaliana* cationic amino acid transporter (GenBank Acc. No.: X92657) or for the *Arabidopsis thaliana* monosaccharide transporter (Gen-Bank Acc. No.: AJ002399) or functional equivalents thereof.

7. Expression of genes which bring about an accumulation of fine chemicals, such as of tocopherols, tocotrienols, phenylpropanoids, isoprenoids or carotenoids, in the flower. Examples which may be mentioned are the deoxyxylulose-5-phosphate synthases, phytoene synthases, lycopene β-cyclases and the β-carotene ketolases. Preference is given to nucleic acids which code for the Haematoccus pluvialis NIES-144 (Acc. No. D45881) ketolase or functional equivalents thereof.

8. Modification of wax ester formation or of the composition of the deposited oligosaccharides to improve protection against environmental effects or to improve digestibility on use in animal or human foods. An example which may be mentioned is overexpression of endo-xyloglucan transferase. Preference is given to nucleic acids which code for the *Arabidopsis thaliana* endo-xyloglucan transferase (EXGT-Al) (Gen-Bank Acc. No.:AF163819) or functional equivalents thereof.

9. Expression of genes, DNA binding proteins, dsRNA and antisense constructions for altering the flower morphology, the time of flowering and the flower senescence, and the flower metabolism. Preference is given to constructions which increase the number of petals, e.g. through down regulation of AGAMOUS and its homologous genes (Yanofsky M F et al. (1990) Nature 346:35-39), make the time of flowering earlier, e.g. through down regulation of FLOWERING LOCUS C (FLC) (Tadege M et al. (2001) Plant J 28(5):545-53) or later, e.g. through overexpression of FLC, and delay senescence, e.g. through conferring a flower-specific ethylene insensitivity.

10. Generation of sterile plants by preventing pollenation and/or germination by means of the expression of a suitable inhibitor, for example of a toxin, in flowers.

11. Production of nutraceuticals such as, for example
    a) carotenoids and/or phenylpropanoids e.g. through optimization of the flowers' own metabolic pathways, e.g. through expression of enzymes and regulators of isoprenoid biosynthesis. Preference is given to nucleic acids which code for the *Arabidopsis thaliana* chalcone synthase (GenBank Acc. No.: M20308), the *Arabidopsis thaliana* 6-4 photolyase (GenBank Acc. No.: BAB00748) or the *Arabidopsis thaliana* blue light photoreceptor/photolyase homolog (PHH1) (GenBank Acc. No.: U62549) or functional equivalents thereof. Preference is likewise given to nucleic acids which code for enzymes and regulators of isoprenoid biosynthesis such as the deoxyxylulose-5-phosphate synthases and of carotenoid biosynthesis such as the phytoene synthases, lycopene cyclases and ketolases, such as of tocopherols, tocotrienols, phenylpropanoids, isoprenoids or carotenoids, in the flower. Examples which may be mentioned are the deoxyxylulose-5-phosphate synthases, phytoene synthases, lycopene cyclases and the carotene ketolases. Particular preference is given to nucleic acids which code for the Haematoccus pluvialis, NIES-144 (Acc. No. D45881) ketolase or functional equivalents.
    b) polyunsaturated fatty acids such as, for example, arachidonic acid or EPA (eicosapentaenoic acid) or DHA (docosahexaenoic acid) through expression of fatty acid elongases and/or desaturases or production of proteins having improved nutritional value, such as, for example, having a high content of essential amino acids (e.g. the methionine-rich 2S albumin gene of the Brazil nut). Preference is given to nucleic acids which code for the *Bertholletia excelsa* methionine-rich 2S albumin (GenBank Acc. No.: AB044391), the *Physcomitrella patens* Δ6-acyl lipid desaturase (GenBank Acc. No.: AJ222980; Girke et al. (1998) Plant J 15:39-48), the *Mortierella alpina* Δ6-desaturase (Sakura-dani et al 1999 Gene 238: 445-453), the *Caenorhabditis elegans* Δ5-desaturase (Michaelson et al. (1998) FEBS Letters 439:215-218), the *Caenorhabditis elegans* Δ5-fatty-acid desaturase (des-5) (GenBank Acc. No.: AF078796), the *Mortierella alpina* Δ5-desaturase (Michaelson et al. J Biol Chem 273:19055-19059), the *Caenorhabditis elegans* Δ6-elongase (Beaudoin et al. (2000) Proc Natl. Acad. Sci. 97:6421-6426), the *Physcomitrella patens* Δ6-elongase (Zank et al. (2000,) Biochemical Society Transactions 28:654-657) or functional equivalents thereof.

12. Production of pharmaceuticals such as, for example, antibodies, vaccines, hormones and/or antibiotics as described, for example, in Hood E E & Jilka J M (1999) Curr Opin Biotechnol 10(4):382-6; Ma J K & Vine N D (1999) CurrTop Microbiol Immunol 236:275-92.

Further examples of advantageous genes are mentioned for example in Dunwell J M (2000) Transgenic approaches to crop improvement. J Exp Bot. 51 Spec No:487-96.

A further aspect of the invention relates to the use of the transgenic organisms of the invention described above, and of the cells, cell cultures, parts—such as, for example, in the case of transgenic plant organisms roots, leaves etc.—and transgenic propagation material such as seeds or fruits, derived therefrom for producing human or animal foods, pharmaceuticals or fine chemicals.

Preference is further given to a method for the recombinant production of pharmaceuticals or fine chemicals in host organisms, where a host organism is transformed with one of the expression cassettes described above, and this expression cassette comprises one or more structural genes which code for the desired fine chemical, or catalyze the biosynthesis thereof, the transformed host organism is cultivated, and the desired fine chemical is isolated from the cultivation medium. This method can be applied widely to fine chemicals such as enzymes, vitamins, amino acids, sugars, fatty acids, natural and synthetic flavorings, aromatizing substances and colorants. Production of tocopherols and tocotrienols, and carotenoids such as, for example, astaxanthin is particularly preferred. Cultivation of the transformed host organisms and isolation from the host organisms or from the cultivation medium take place by methods known to the skilled worker. The production of pharmaceuticals such as, for example, antibodies or vaccines is described in Hood E E & Jilka J M (1999) Curr Opin Biotechnol 10 (4)382-6; Ma J K & Vine N D (1999) Curr Top Microbiol Immunol 236:275-92.

Sequences
1. SEQ ID NO: 1 2051 bp fragment of promoter (and if appropriate 5' untranslated region of the *Arabidopsis thaliana* gene locus At3g01980 (76L promoter)
2. SEQ ID NO: 2 2192 bp fragment of promoter (and if appropriate 5' untranslated region of the *Arabidopsis thaliana* gene locus At1g63140 (84L promotor)

-continued

3. SEQ ID NO: 3 Functionally equivalent fragment (1045 bp) of promoter (and if appropriate 5' untranslated region of *Arabidopsis thaliana* gene locus At3g01980 (76S promoter)
4. SEQ ID NO: 4 Functionally equivalent fragment (1109 bp) of promoter (and if appropriate 5' untranslated region of *Arabidopsis thaliana* gene locus At1g63140 (84L promoter)
5. Seq ID No: 5 Oligonucleotide primer 76sSmaI
5'-CCCGGGTGCCAAAGTAACTCTTTAT-3'
6. Seq ID No: 6 Oligonucleotide primer 76assSalI
5'-GTCGACAGGTGCATGACCAAGTAAC-3'
7. Seq ID No: 7 Oligonucleotide primer 76aslSalI
5'-GTCGACTATCCTCTGCGCAATGAAT-3'
8. Seq ID No: 8 Oligonucleotide primer 84sSmaI
5'-CCCGGGAAATCGAGAAAGATAGGTA-3'
9. Seq ID No: 9 Oligonucleotide primer 84assSalI
5'-GTCGACAAAGGGTTATAGGAGACTG-3'
10. Seq ID No: 10 Oligonucleotide primer 84aslSalI
5'-GTCGACCATGTTTCAGAGGATATGT-3'
11. SEQ ID NO: 11 Nucleic acid sequence (cDNA) encoding the gene product of the *Arabidopsis thaliana* gene locus At3g01980
12. SEQ ID NO: 12 Amino acid sequence encoding the gene product of the *Arabidopsis thaliana* gene locus At3g01980
13. SEQ ID NO: 13 Nucleic acid sequence (cDNA) encoding the gene product of the *Arabidopsis thaliana* gene locus At1g63140
14. SEQ ID NO: 14 Amino acid sequence encoding the gene product of the *Arabidopsis thaliana* gene locus At1g63140
15. SEQ ID NO: 15 Nucleic acid sequence (cDNA) encoding the oilseed rape homolog (H2) of the At3g01980 gene product
16. SEQ ID NO: 16 Amino acid sequence encoding the oilseed rape homolog (H2) of the At3g01980 gene product
17. SEQ ID NO: 17 Nucleic acid sequence (cDNA) encoding the oilseed rape homolog (H3) of the At3g01980 gene product
18. SEQ ID NO: 18 Amino acid sequence encoding the oilseed rape homolog (H3) of the At3g01980 gene product
19. SEQ ID NO: 19 Nucleic acid sequence (cDNA) encoding the oilseed rape homolog (H4) of the At1g63140 gene product -continued

| | | |
|---|---|---|
| 20. | SEQ ID NO: 20 | Amino acid sequence encoding the oilseed rape homolog (H4) of the At1g63140 gene product |
| 21. | SEQ ID NO: 21 | Nucleic acid sequence (cDNA) encoding the oilseed rape homolog (H5) of the At1g63140 gene product |
| 22. | SEQ ID NO: 22 | Amino acid sequence encoding the oilseed rape homolog (H5) of the At1g63140 gene product |
| 23.-32 | SEQ ID NO: 23 bis 32: | Sequence motifs for proteins with specific expression in the nonreproductive floral tissues. |
| 33. | Seq ID No: 33 | Oligonucleotide primer GUS for 5'-cac ttt tcc cgg caa taa cat-3' |
| 34. | Seq ID No: 34 | Oligonucleotide primer GUS rev 5'-atc agg aag tga tgg agc atc-3' |
| 35. | Seq ID No: 35 | Oligonucleotide primer TUB for 5'-gac cct gtc cca cct cca a-3' |
| 36. | Seq ID No: 36 | Oligonucleotide primer TUB rev 5'-tga gaa ctg cga ttg ttt gca-3' |

FIGURES

The general abbreviations used in the following figures have the following meaning:
GUS: reporter gene (bacterial β-glucuronidase)
Int: Intron
NosT: nopaline synthase (NOS) terminator sequence
NptII: BASTA resistance
NosP: nopaline synthase (NOS) promoter sequence
AadA: bacterial spectinomycin resistance 1. FIG. 1: Diagrammatic representation of the vector pSUN3-76L-GUS. Further abbreviations have the following meaning:
76L: 76L promoter of SEQ ID NO:1

Figure 2:
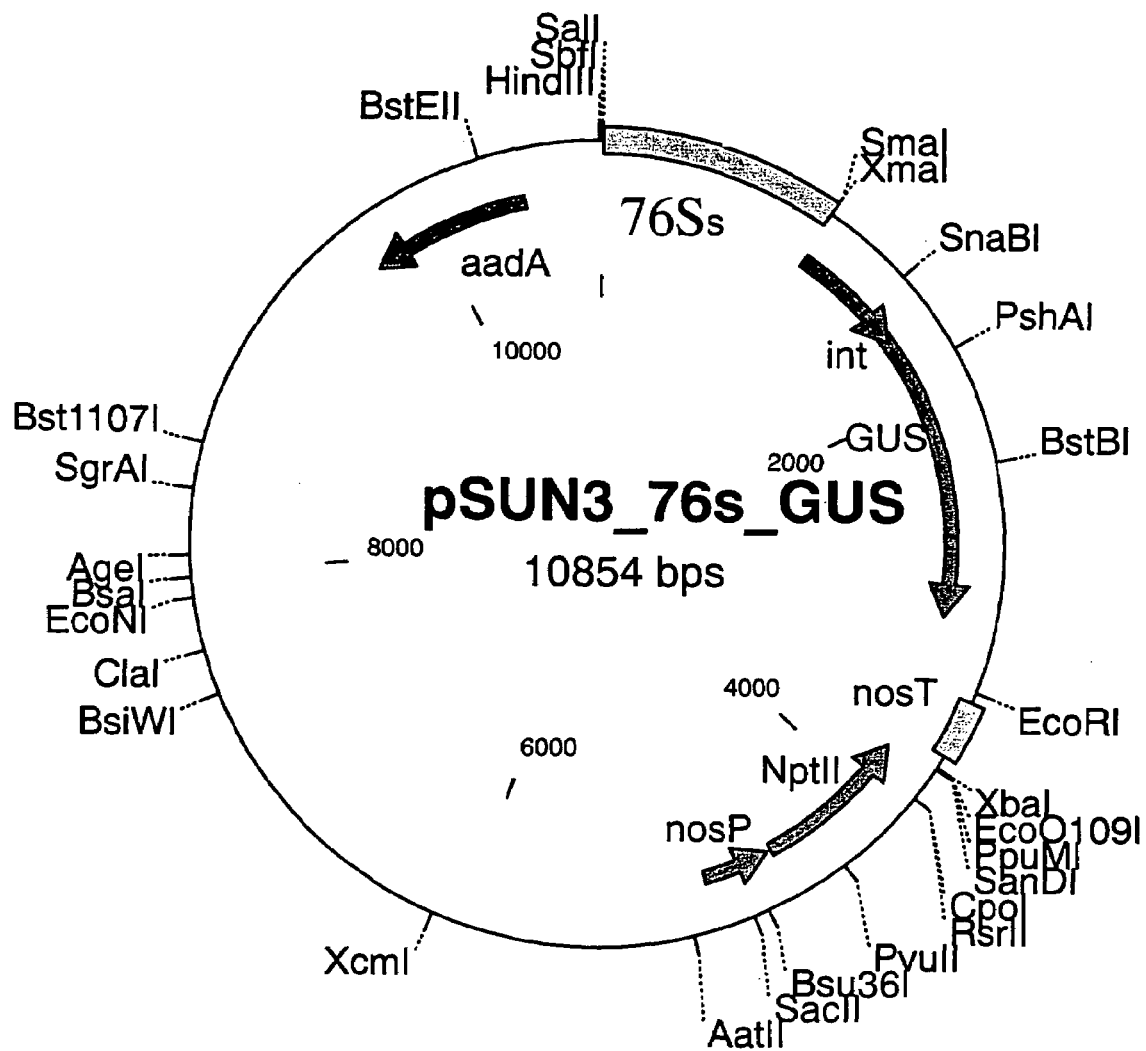

2. FIG. 2: Diagrammatic representation of the vector pSUN3-76S-GUS. Further abbreviations have the following meaning:
76S: 76S promoter of SEQ ID NO: 3

Figure 3:
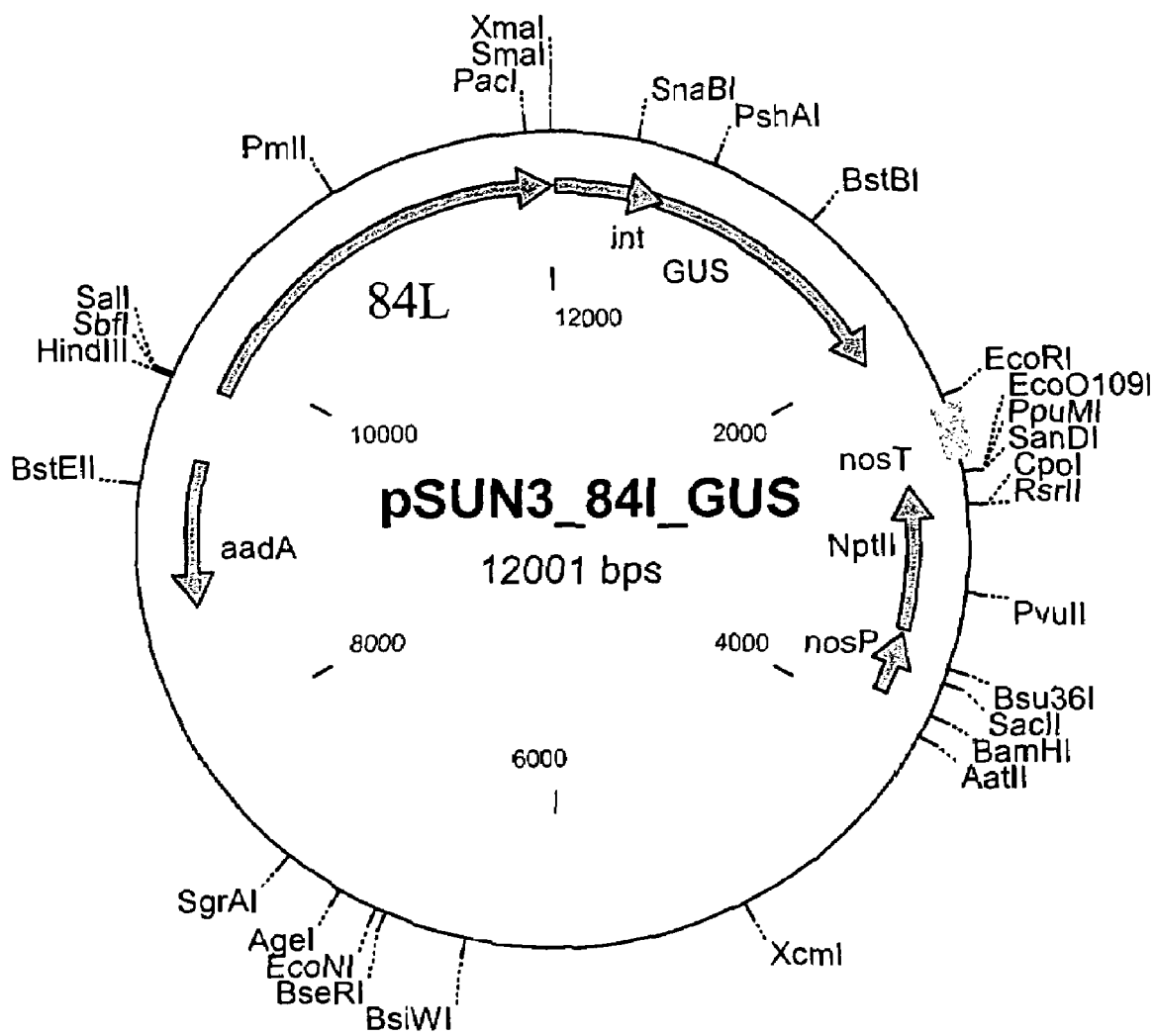

3. FIG. 3: Diagrammatic representation of the vector pSUN3-84L-GUS. Further abbreviations have the following meaning:
84L: 84L promoter of SEQ ID NO: 2

Figure 4:
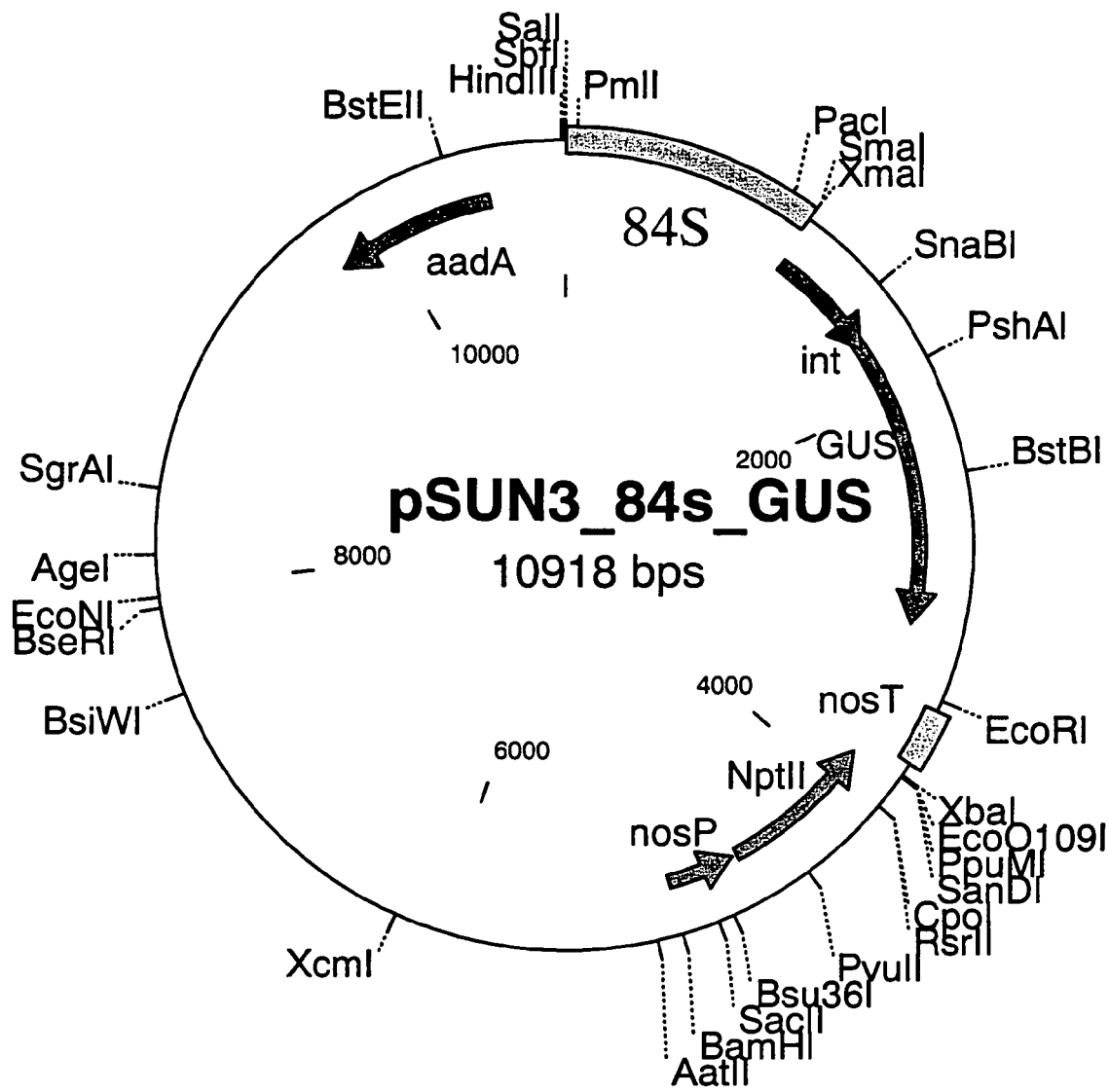

4. FIG. 4: Diagrammatic representation of the vector pSUN3-84S-GUS. Further abbreviations have the following meaning:
84S: 84S promoter of SEQ ID NO: 4

Figure 5:
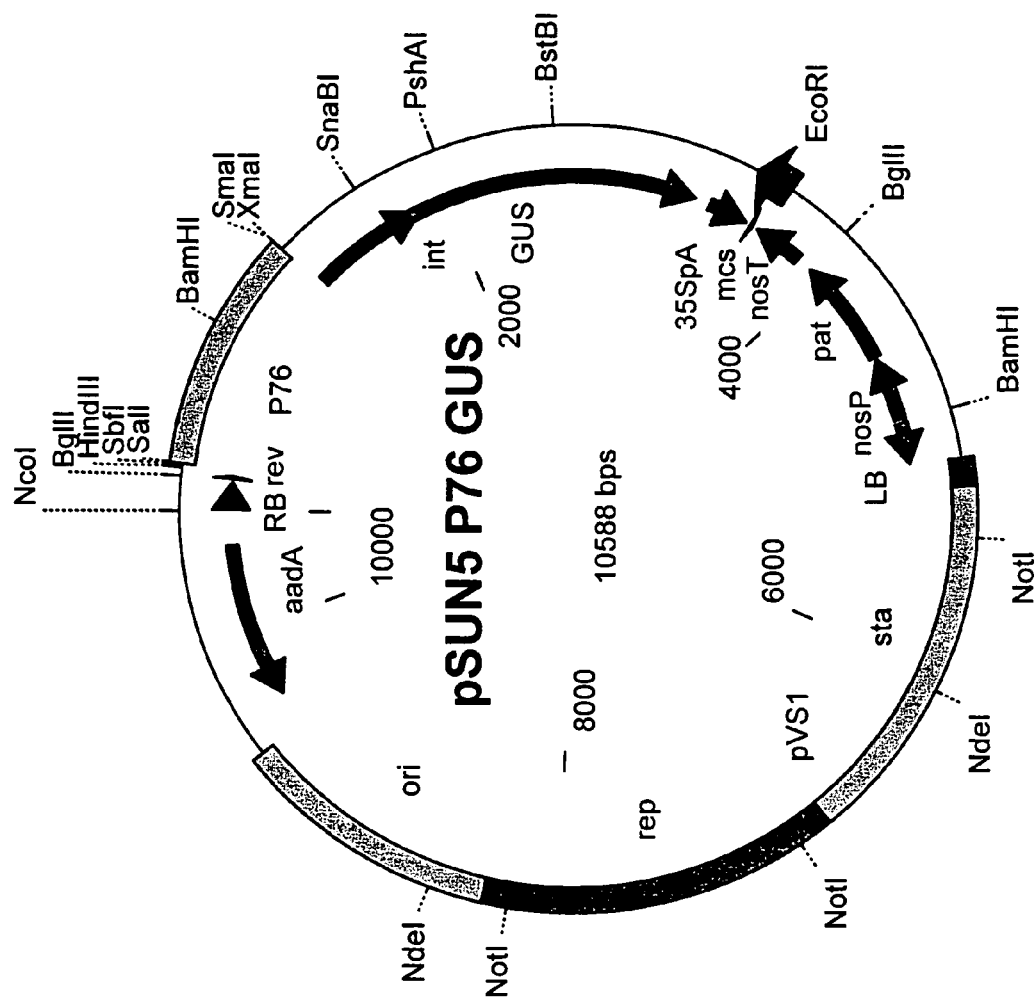

5. FIG. 5: Diagrammatic representation of the vector pSUN5-P76-GUS. Further abbreviations have the following meaning:
P76: 76S promoter of SEQ ID NO: 3

6. FIG. 6: The expression patterns of the promoters 76 (A) and 84 (B) in the flower of *Arabidopsis thaliana* are shown. White/pale gray areas indicate tissues without promoter activity.

7. FIG. 7: The expression patterns of the promoters 76 (A) and 84 (B) in the inflorescences and leaves of *Arabidopsis thaliana* are shown. White/pale gray areas indicate tissues without promoter activity.

Figure 8:
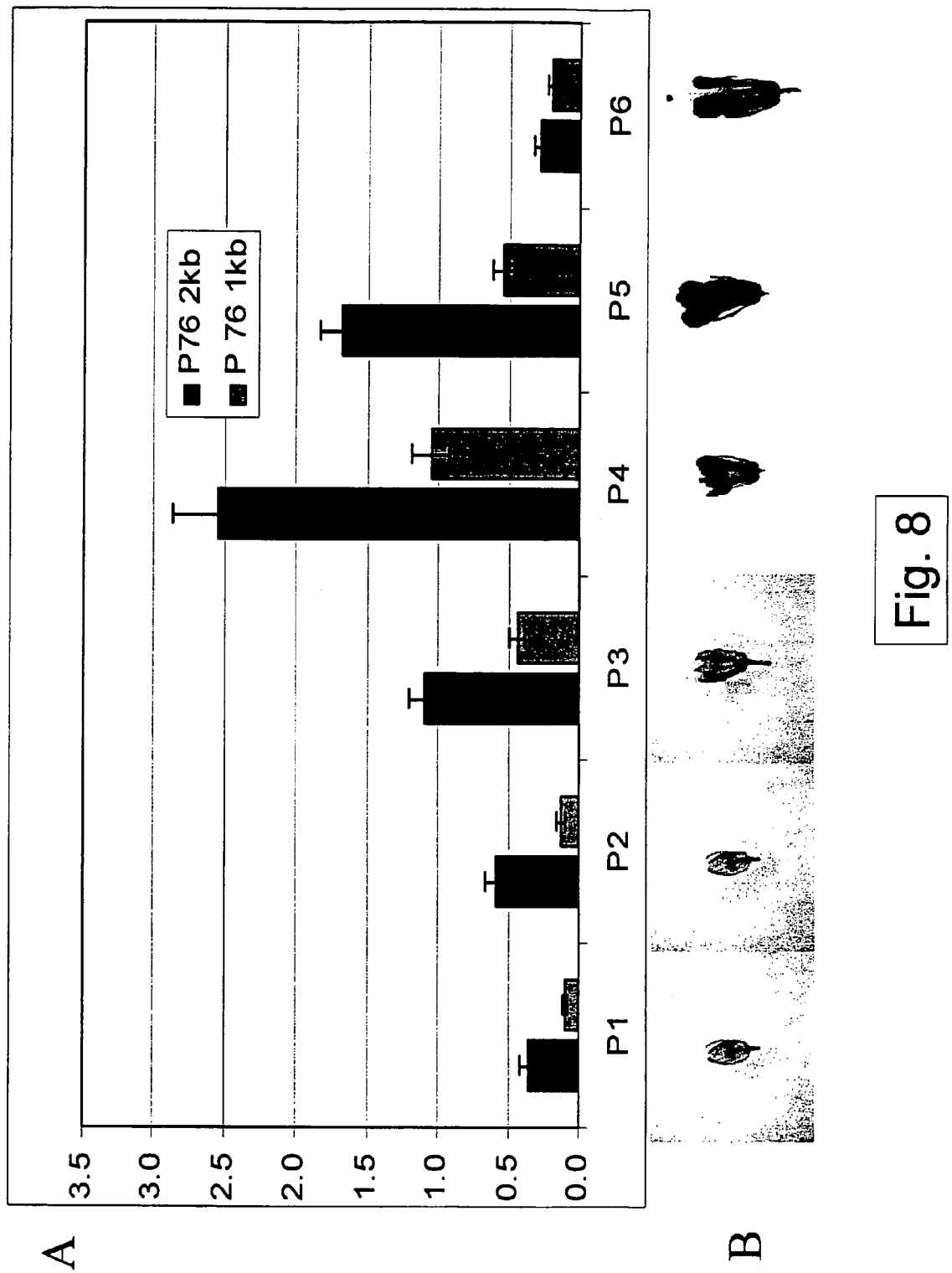

8. FIG. 8: The resolution of the promoter activity of the promoter 76 over time during the floral development of *Arabidopsis thaliana* is shown. A: β-glucuronidase mRNA quantities in six stages of the floral development (P1 to P6) of *Arabidopsis thaliana* for the promoter 76. The data were determined by means of quantiative "real time" PCR and standardized with the 1 kb P76 promoter during flowering stage P4 (to this end, the value in question was set equal to 1). B: The points in time of the development of the *Arabidopsis* flowers which correspond to the flowering stages P1 to P6 are shown.

Figure 9:
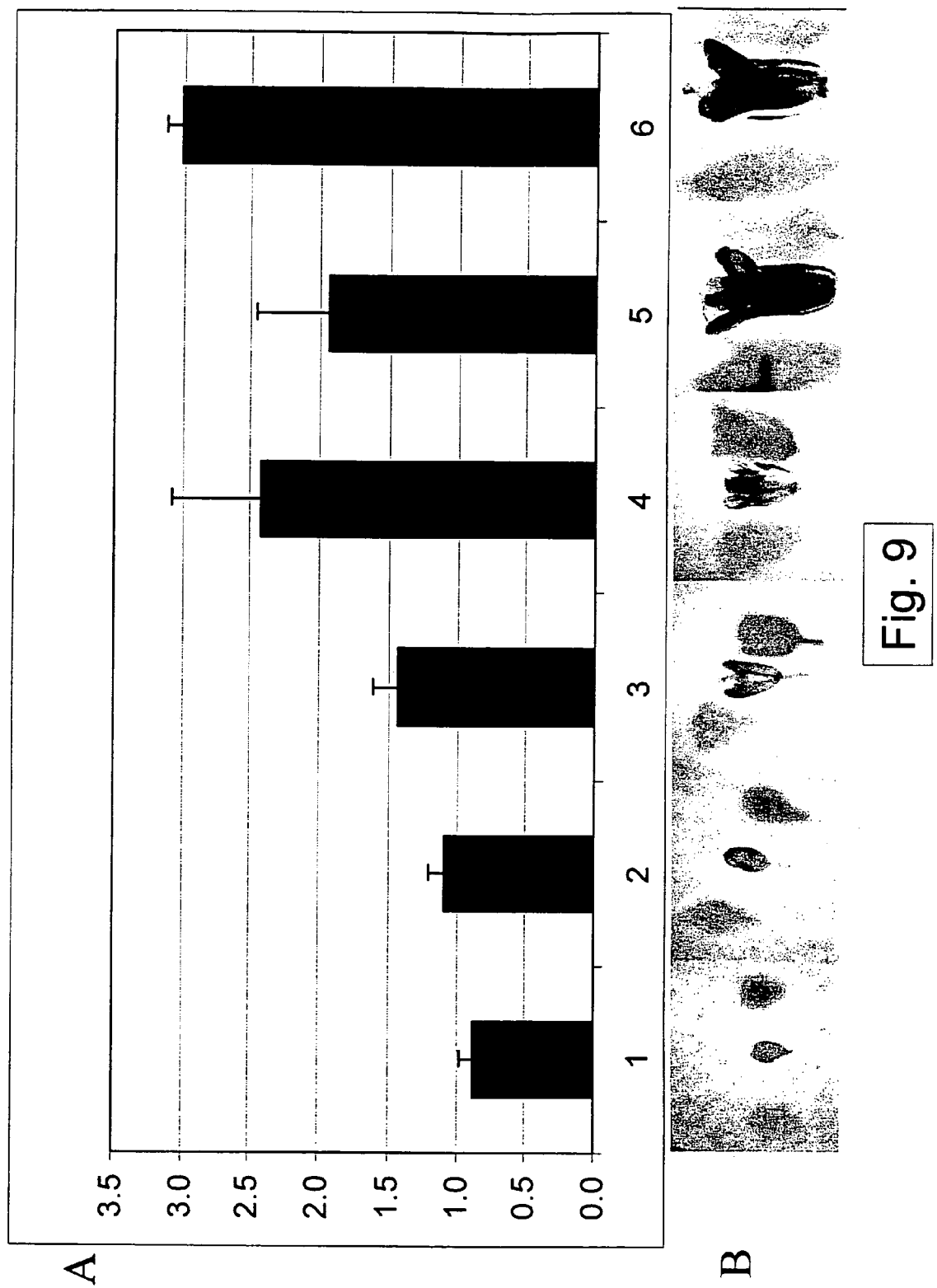

9. FIG. 9: The resolution of the promoter activity of the promoter 84 over time during the floral development of *Arabidopsis thaliana* is shown. A: β-glucuronidase mRNA quantities in six stages of the floral development (P1 to P6) of *Arabidopsis thaliana* for the promoter 84. the data were determined by means of quantiative "real time" PCR and standardized with the during flowering stage P2 (to this end, the value in question was set equal to 1). B: The points in time of the development of the *Arabidopsis* flowers which correspond to the flowering stages P1 to P6 are shown.

Figure 10:
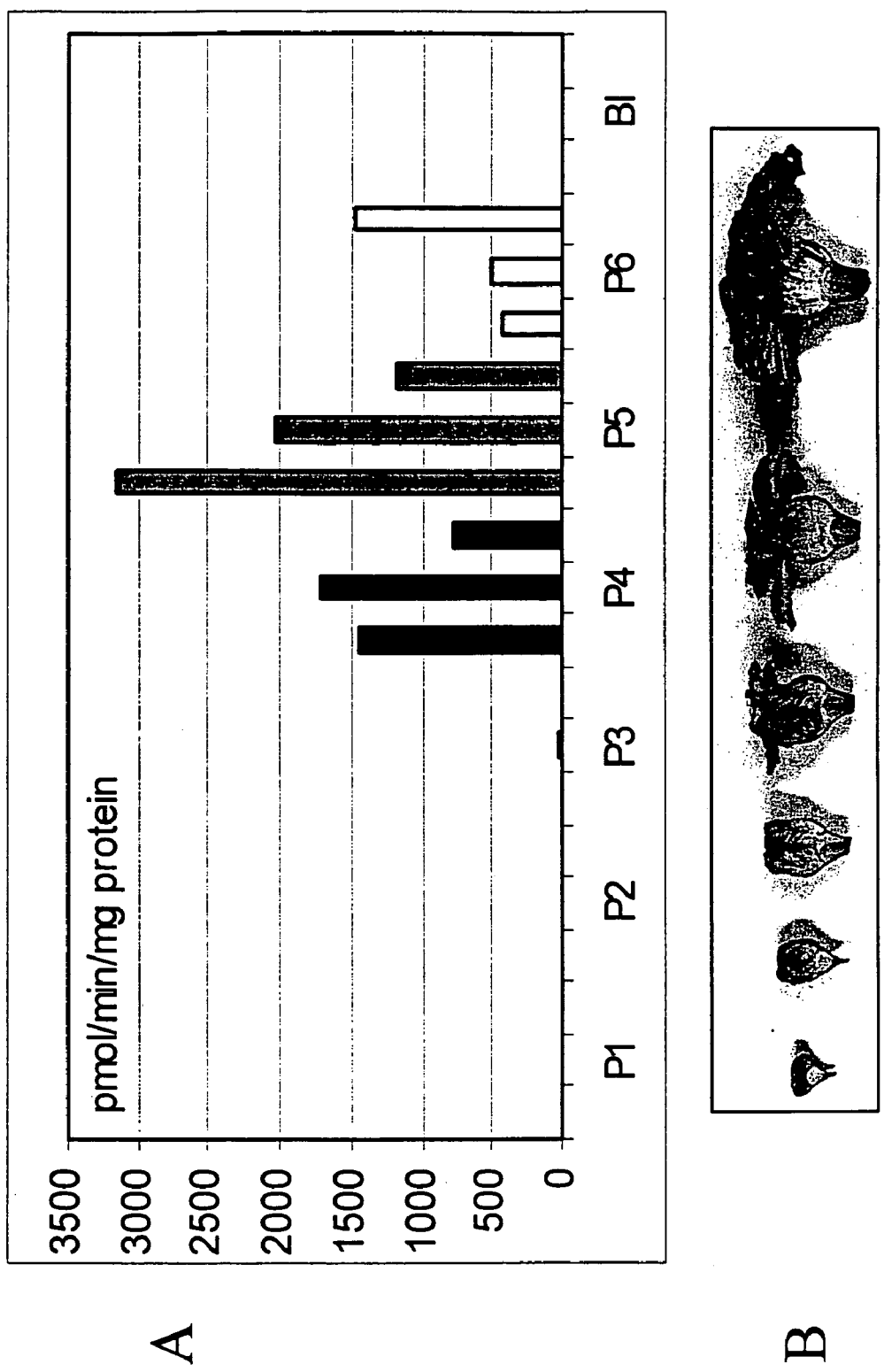

10. FIG. 10: A resolution of the promoter activity of the promoter 76 over time during the floral development of Tagetes erecta are shown. A: β-glucuronidase enzyme activity (shown in pmol of methyl umbelliferon/min/mg protein) during six stages of the floral development (P1 to P6) of Tagetes erecta for the promoter 76. In each case 3 individual measurements are shown (black bars, gray bars, white bars).
B: The points in time of the development of the Tagetes flowers which correspond to the flowering stages P1 to P6 are shown.

11. FIG. 11: The resolution of the promoter activity of the promoter 76 over time during the floral development of Tagetes erecta is shown. A: β-glucuronidase mRNA quantities in six stages of the floral development (P1 to P6) of Tagetes erecta for the promoter 76. The data were determined by means of quantiative "real time" PCR and standardized with the during flowering stage P4 (to this end, the value in question was set equal to 1). B: The points in time of the development of the Tagetes flowers which correspond to the flowering stages P1 to P6 are shown.

12. FIG. 12: Protein sequence alignment between the SEQ ID NO: 12 amino acid sequence (cDNA) encoding the gene product of the *Arabidopsis thaliana* gene locus At3g01980 and a cDNA clone from a *Brassica napus* floral cDNA library.

13. FIG. 13: Protein sequence alignment between the SEQ ID NO: 14 amino acid sequence (cDNA) encoding the gene product of the *Arabidopsis thaliana* gene locus At1g63140 and a cDNA clone from a *Brassica napus* floral cDNA library.

Figure 14:
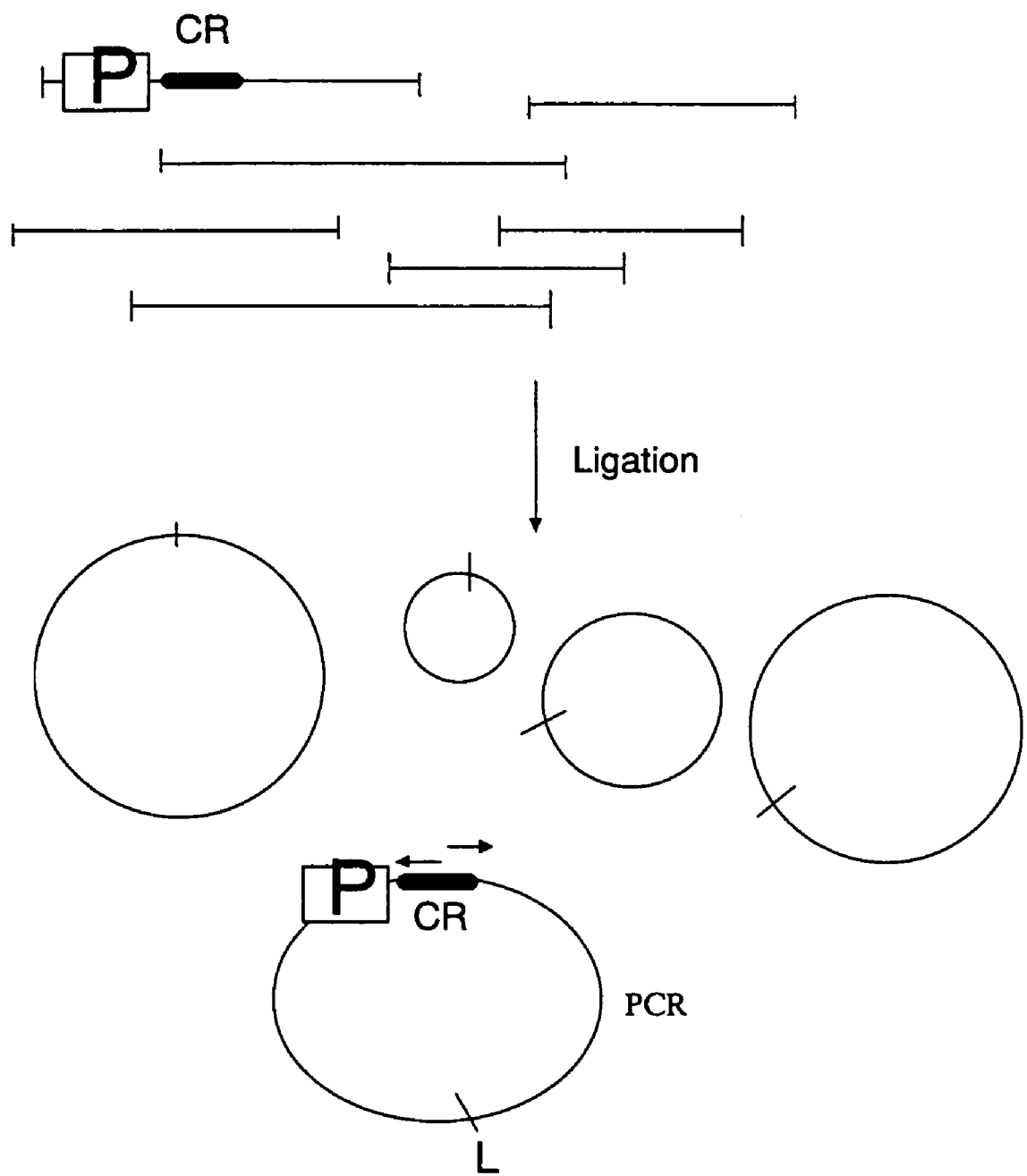

14. FIG. 14: diagrammatic representation of the inverse PCR ("iPCR"). For the "iPCR", genomic DNA of a target organism having the promoter sequence to be isolated is completely digested with a given restriction enzyme, and then the individual fragments are religated, i.e. connected together to form a circular molecule, in a diluted mixture. The large number of resulting circular DNA molecules includes those comprising the known sequence (i.e. the sequence coding for a homologous protein). The circular molecule can be amplified, starting therefrom, by means of PCR using a primer pair in which both primers are able to anneal to the known sequence segment. Abbreviations: P—promoter sequence; CR—coding region; L—ligation site; PCR—polymerase chain reaction. Arrows represent the binding site of potential oligonucleotide primers in the area of the coding region.

EXAMPLES

General Methods:

Oligonucleotides can be chemically synthesized for example in a known manner by the phosphoramidite method (Voet & Voet (1995), $2^{nd}$ edition, Wiley Press New York, pages 896-897). The cloning steps carried out for the purposes of the present invention, such as, for example, restriction cleavages, agarose gel electrophoresis, purification of DNA fragments, transfer of nucleic acids to nitrocellulose and nylon membranes, linkage of DNA fragments, transformation of E. coli cells, culturing of bacteria, replication of phages and sequence analysis of recombinant DNA, are carried out as described in Sambrook et al. (1989) Cold Spring Harbor Laboratory Press; ISBN 0-87969-309-6. Recombinant DNA molecules are sequenced by the method of Sanger (Sanger et al. (1977) Pro Natl Acad Sci USA 74:5463-5467) using an ABI laser fluorescence DNA sequencer.

To generate transgenic *Arabidopsis* plants, *Agrobacterium tumefaciens* (strain C58C1 pMP90) is transformed with various promoter GUS vector constructs. The agrobacterial strains are subsequently used for the generation of transgenic plants. To this end, an individual transformed *Agrobacterium* colony is incubated in a 4 ml culture (medium: YEB medium supplemented with 50 µg/ml kanamycin and 25 µg/ml of rifampicin overnight at 28° C. This culture is subsequently used to inoculate a 400 ml culture in the same medium, and this culture is incubated overnight (28° C., 220 rpm) and spun down (GSA rotor, 8000 rpm, 20 min). The pellet is resuspended in infiltration medium (1/2 MS medium; 0.5 g/l MES, pH 5.8; 50 g/l sucrose). The suspension is introduced into a plant box (Duchefa) and 100 ml of SILVET L-77 (polyalkylene oxide-modified heptamethyltrisiloxane; Osi Special-ties Inc., Cat. P030196) was added to a final concentration of 0.02%. In a desiccator, the plant box together with 8 to 12 plants is exposed to a vacuum for 10 to 15 minutes, followed by spontaneous aeration. This is repeated 2 to 3 times. Thereafter, all the plants are planted into plant pots containing moist soil and grown under long-day conditions (illumination for 16 hours) (daytime temperature 22 to 24° C., nighttime temperature 19° C.; relative atmospheric humidity 65%). The seeds are harvested after 6 weeks.

Example 1

Growth Conditions of the Plants for Tissue-specific RT-PCR Analysis

To obtain 4- or 7-day-old seedlings, in each case approximately 400 seeds (*Arabidopsis thaliana* ecotype Columbia) are surface-sterilized for 2 minutes with an 80% strength ethanol solution, treated for 5 minutes with sodium hypochlorite solution (0.5% v/v), washed three times with distilled water and incubated at 4° C. for 4 days to ensure uniform germination. Thereafter, the seeds are incubated on Petri dishes comprising MS medium (Sigma M5519) with addition of 1% sucrose, 0.5 g/l MES (Sigma M8652), 0.8% Difco-Bacto agar (Difco 0140-01), pH 5.7. The seedlings are grown in a 16-hour-light/8-hour-dark photoperiod (Philips 58W/33 white-light lamps) at 22° C. and harvested after 4 and 7 days, respectively, after the beginning of the germination phase.

To obtain roots, 100 seeds are sterilized as described above, incubated for 4 days at 4° C. and then grown in 250 ml flasks comprising MS medium (Sigma M5519) with addition of a further 3% sucrose and 0.5 g/l MES (Sigma M8652), pH 5.7. The seedlings are grown in a 16-hour-light/8-hour-dark photoperiod (Philips 58W/33 white-light lamps) at 22° C., 120 rpm, and harvested after 3 weeks. For all other plant organs which are used, the seeds are sown on standard soil (type VM, Manna-Italia, Via S. Giacomo 42, 39050 San Giacomo/Laives, Bolzano, Italy), incubated for 4 days at 4° C. to ensure uniform germination and then grown in a 16-hour-light/8-hour-dark photoperiod (OSRAM Lumi-lux Daylight 36W/12 fluorescent tubes) at 22° C. Young rosette leaves are harvested in the 8-leaf stage (after 3 weeks), and mature rosette leaves are harvested after 8 weeks shortly before stems are formed. Inflorescences (apices) of the shooting stems are harvested shortly after shooting. Stems, stem leaves and flower buds are harvested at developmental stage 12 (Bowmann J (ed.), *Arabidopsis*, Atlas of Morphology, Springer New York, 1995) prior to stamen development. Opened flowers are harvested at stage 14 immediately after stamen development. Wilting flowers are harvested at stage 15 to 16. The green and yellow pods which were used were 10 to 13 mm in length.

Example 2

RNA Extraction and cDNA Synthesis

Total RNA is isolated from the plant organs described in Example 1 at various points in time of the development, as described (Prescott A, Martin C (1987) Plant Mol Biol Rep 4:219-224). The reverse-transcriptase polymerase chain reaction (RT-PCR) is used to detect the cDNA of the gene transcripts of At3g01980 and At1G63140. Prior to cDNA synthesis, all RNA samples are treated with DNaseI (15 units, Boehringer, Mannheim). The first-strand cDNA synthesis is carried out starting from 6 µg of total RNA with an oligo-(dT) primer and RT Superscript™ II enzyme (300 units) following the manufacturer's instructions in a total volume of 20 µl (Life Technologies, Gaithersburg, Md.). To this end, 150 ng of "Random Hexamer Primer" are added in a final volume of 12 µl. The mixture is heated for 10 minutes at 70° C. and subsequently immediately cooled on ice. Then, 4 µl of the 5× first-strand buffer, 2 µl of 0.1 M DTT, 1 µl of 10 mM dNTP-mix (in each case 10 mM dATP, dCTP, dGTP and dTTP) and RNase inhibitor (5 units, Böhringer Mannheim) are added. The mixture is heated for 2 minutes at 42° C., RT Superscript™ II enzyme (300 units, Life Technologies) is added, and the mixture is incubated for 50 minutes at 42° C.

Example 3

Detection of the Tissue-specific Expression

To determine the properties of the promoter and to identify the essential elements thereof, which account for its tissue specificity, it is necessary to place the promoter itself and various fragments thereof before what is known as a reporter gene, which makes possible a determination of the expression activity. An example which may be mentioned is the bacterial β-glucuronidase (Jefferson et al. (1987) EMBO J 6:390'-3907). The β-glucuronidase activity can be determined in planta by means of a chromogenic substrate such as 5-bromo-4-chloro-3-indolyl-β-D-glucuronic acid in an activity stain (Jefferson et al. (1987) Plant Mol Biol Rep 5:387-405). To study the tissue specificity, the plant tissue is disected, embedded, stained and analyzed as described (for example Bäumlein H et al. (1991) Mol Gen Genet 225:121-128).

MUG (methylumbelliferylglucuronide) is used as substrate for the quantitative determination of the β-glucuronidase activity; it is cleaved into MU (methylumbelliferone) and glucuronic acid. Under alkaline conditions, this cleavage can be monitored quantitatively by fluorometry (excitation at 365 nm, measurement of the emission at 455 nm; SpectroFluorimeter Thermo Life Sciences Fluoroscan) as described (Bustos M M et al. (1989) Plant Gell 1:839-853).

Example 4

Cloning the Promoters

To isolate the complete promoters of Seq ID NO: 1 or 2, genomic DNA is extracted from *Arabidopsis thaliana* (ectotype Landsberg erecta) as described (Galbiati M et al. Funct Integr Genomics 2000, 20 1:25-34). The isolated DNA is employed as template DNA in a PCR, using the following primers:

| Promoter | Forward primer | Reverse primer |
| --- | --- | --- |
| 761 (SEQ ID NO: 2) | SEQ ID NO: 5 (76s) | SEQ ID NO: 7 (76asl) |
| 841 (SEQ ID NO: 3) | SEQ ID NO: 8 (84s) | SEQ ID NO: 10 (84asl) |
| 76s (SEQ ID NO: 4) | SEQ ID NO: 5 (76s) | SEQ ID NO: 6 (76ass) |
| 84s (SEQ ID NO: 5) | SEQ ID NO: 8 (84s) | SEQ ID NO: 9 (84ass) |

The amplification is carried out as follows:
80 ng genomic DNA
1× Expand™ Long Template PCR buffer
2.5 mM MgCl2,
350 µM of each dATP, dCTP, dGTP and dTTP
300 nM of each primer—(SEQ ID NO: 5 and 7 for promoter 761 and SEQ ID NO 8 and 10 for promoter 84s)
2.5 units Expand™ Long Template polymerase (Roche Diagnostics).
in a final volume of 25 µl The following temperature program is used (PTC-100TM model QfiV; MJ Research, Inc., Watertown, Mass.):
1 cycle with 120 seconds at 94° C.
35 cycles with 10 seconds at 94° C., 30 seconds at 55° C. and 3 minutes at 68° C.
1 cycle for 30 minutes 45 at 68° C.

The PCR products were cleaved with the restriction endonucleases SmaI and SalI and cloned into the vector pSUN::GUS. The resulting constructs are pSUN3-76L::GUS (FIG. 9), pSUN3-76S::GUS (FIG. 10), pSUN3-84L::GUS (FIG. 11) and pSUN3-84S::GUS (FIG. 11). After these constructs have been stably transformed into *Arabidopsis thaliana*, RNA can be obtained from the various tissues, and the expression of the GUS gene can be shown qualitatively by RT-PCR and quantitatively by means of "Real Time" PCR.

The method for the quantitative "Real Time" PCR is described for example in Bustin S A (2000) J Mol Endocrinol 25(2):169-93.

The Primers

```
GUS for 5'-cac ttt tcc cgg caa taa cat-3'
GUS rev 5'-atc agg aag tga tgg agc atc-3'
``` were used for detecting and quantifying the GUS mRNA. The values were standardized with the constitutively expressed tubulin. To detect and quantify tubulin, the primers

```
TUB for 5'-gac cct gtc cca cct cca a-3'
TUB rev 5'-tga gaa ctg cga ttg ttt gca-3'
``` were used.

Example 5

TAIL-PCR

The "TAIL-PCR" is carried out in accordance with an adapted protocol of the method of Liu et al. (1995) Plant J 8(3):457-463 and Tsugeki et al. (1996) Plant J 10(3):479-489 (cf. FIG. 9). The following mastermix (quantities per reaction mix) is employed for a first PCR reaction:
11 µl steril H₂O (double-distilled)
2 µl primer stock solution of the specific primer 1 (5 mM)
3 µl AD2 primer stock solution (20 mM)
2 µl 10×PCR buffer
2 µl 10×dNTP
0.2 µl Taq polymerase In a PCR vessel, 19 µl of this mastermix are pipetted to 1 µl of a preparation of genomic DNA of the target organism in question (preparation as described by Galbiati M et al. (2000) Funct Integr Genomics 20(1):25-34)) and mixed thoroughly by pipetting.

The primary PCR reaction is carried out under the following conditions:
94° C. for 1 minute
four cycles with 94° C. for 10 seconds, 62° C. for 1 minute and 72° C. for 150 seconds
94° C. for 10 seconds, 25° C. for 3 minutes, 0.2° C./s to 72° C. and 72° C. for 150 seconds
fourteen cycles at 94° C. for 10 seconds, 69° C. for 1 minute, 72° C. for 150 seconds, 94° C. for 10 seconds, 68° C. for 1 minute, 72° C. for 150 seconds, 94° C. for 10 seconds, 44° C. for 1 minute and 72° C. for 150 seconds
72° C. for 5 minutes, then 4° C. until further use.

The product of the PCR reaction is diluted 1:50, and 1 µl of each diluted sample is used for a second PCR reaction (secondary PCR). The following mastermix is employed for this purpose (quantities per reaction mix):
12 µl of sterile H₂O (double distilled)
2 µl 10×PCR buffer (1.5 mM MgCl₂)
2 µl 10×dNTP
2 µl primer stock solution of the specific primer 2 (5 mM)
2 µl AD2 primer stock solution
0.2 µl Taq polymerase In each case 20.2 µl of the second mastermix are added to in each case 1 µl of the 1:50 diluted primary PCR product, and the secondary PCR is carried out under the following conditions:
11 cycles at 94° C. for 10 seconds, 64° C. for 1 minute, 72° C. for 150 seconds, 94° C. for 10 seconds, 64° C. for 1 minute, 72° C. for 150 seconds, 94° C. for 10 seconds, 44° C. for 1 minute, 72° C. for 150 seconds,
72° C. for 5 minutes, then 4° C. until further use.

The product of the PCR reaction is diluted 1:10, and 1 µl of each diluted sample is used for a third PCR reaction (tertiary PCR). The following mastermix is employed for this purpose (quantities per reaction mix):

18 µl of sterile H₂O (double distilled)
3 µl 10×PCR buffer (1.5 mM MgCl₂)
3 µl 10×dNTP
3 µl primer stock solution of the specific primer 3 (5 mM)
3 µl AD2 primer stock solution
0.5 µl Taq polymerase
In each case 30.3 µl of this mastermix are added to in each case
1 µl of the 1:10 diluted secondary PCR product, and the tertiary PCR is carried out under the following conditions:
19 cycles at 94° C. for 15 seconds, 44° C. for 1 minute, 72° C. for 150 seconds,
72° C. for 5 minutes, then 4° C. until further use.

In each case 5 µl of the products of the PCR 1, 2 and 3 of each sample are separated on a 2% strength agarose gel. Those PCR products which, owing to the treated specific primers, show the expected size decrement are, if necessary, purified from the gel, reamplified with the primer pair which was used last, and then sequenced.

Reagents:
Taq polymerase 5U/µl
10×PCR buffer (1.5 mM MgCl₂)
10×dNTP stock solution: 2 mM Primers:
Degenerate random primer (stock solutions 20 µM):

```
AD1:  5'-NTCGA(G/C)T(A/T)T(G/C)G(A/T)GTT-3'

AD2:  5'-NGTCGA(G/C)(A/T)GANA(A/T)GAA-3'

AD5:  5'-(A/T)CAGNTG(A/T)TNGTNCTG-3'
```

Example 6

Inverse PCR (iPCR) for the Amplification of Insert-flanking DNA

The "iPCR" is carried out in accordance with an adapted protocol of the method of Long et al. (1993) PNAS 90:10370 (cf. FIG. 8):
1. Restriction of approx. 2 µg of genomic DNA with BstYI for approximately 2 hours at 37° C. in a total volume of 50 µl.
2. Ligation of 25 µl of the restriction mix with 3U T4-DNA ligase at 15° C. overnight in a total volume of 300 µl.
3. Phenol/chloroform extraction and subsequent chloroform extraction of the ligation mix. After ethanol precipitation, take up DNA in 10 µl of sterile H₂O (double-distilled).
4. Employ 2.5 µl of the DNA solution for the PCR
   Reaction mix:
   2.5 µl of the DNA solution
   10 µl 10×PCR buffer
   2 µl dNTP (mixture of 10 mM each)
   5 µl primer 1 (25 pmol)
   5 µl primer 2 (25 pmol)
   1,5 µl Taq polymerase
   74 µl H₂O (double-distilled, sterile)
   to a total volume of 100 µl
   PCR protocol: 4 minutes at 94° C. Then 35 cycles with 1 minute at 94° C., 2 minutes at 55° C. and 3 minutes at 72° C. Finally, 8 minutes at 72° C., then 4° C. until further use.

The PCR product is checked by gel electrophoresis, purified and subsequently sequenced as PCR product.

Example 6

Production of Transgenic Tagetes Plants

Tagetes seeds are sterilized and placed on germination medium (MS medium; Murashige & Skoog (1962) Physiol Plant 15:473-497; pH 5.8, 2% sucrose). Germination takes place in a temperature/light/time interval of 18 to 28° C./20 to 200 µE/3 to 16 weeks, but preferably at 21° C., 20 to 70 µE, for 4 to 8 weeks.

All leaves of the plants which have developed in vitro by then are harvested and cut transverse to the central vein. The leaf explants resulting therefrom, with a size of 10 to 60 mm², are stored during the preparation in liquid MS medium at room temperature for not more than 2 h.

Any *Agrobacterium tumefaciens* strain, but preferably a supervirulent strain such as, for example, EHA105 with an appropriate binary plasmid, which may harbor a selection marker gene (preferably bar or pat) and one or more trait or reporter genes (for example pS5KETO2 and pS5AP3PKETO2), is cultivated overnight and used for cocultivation with the leaf material. The bacterial strain can be cultured as follows: a single colony of the appropriate strain is inoculated in YEB (0.1% yeast extract, 0.5% beef extract, 0.5% peptone, 0.5% sucrose, 0.5% magnesium sulfate× 7H₂O) with 25 mg/l kanamycin and cultured at 28° C. for 16 to 20 h. The bacterial suspension is then harvested by centrifugation at 6000 g for 10 min, and resuspended in liquid MS medium so as to result in an OD₆₀₀ of about 0.1 to 0.8. This suspension is used for the cocultivaation together with the leaf material.

Immediately before the cocultivation, the MS medium in which the leaves have been stored is replaced by the bacterial suspension. Incubation of the leaves in the agrobacterial suspension took place at room temperature with gentle shaking for 30 min. The infected explants are then put on an MS medium solidified with agar (e.g. 0.8% plant agar (Duchefa, NL)), with growth regulators such as, for example, 3 mg/l benzylaminopurine (BAP) and 1 mg/l indolylacetic acid (IAA). The orientation of the leaves on the medium is immaterial. Cultivation of the explants takes place for 1 to 8 days, but preferably for 6 days, during which the following conditions can be used: light intensity: 30 to 80 µmol/m²×sec, temperature: 22 to 24° C., 16/18-hour photoperiod. The cocultivated explants are then transferred to fresh MS medium, preferably with the same growth regulators, this second medium additionally containing an antibiotic to suppress bacterial growth. Timentin in a concentration of 200 to 500 mg/l is very suitable for this purpose. The second selective component employed is one for selecting for successful transformation. Phosphinothricin in a concentration of 1 to 5 mg/l selects very efficiently, but other selective components according to the method to be used are also conceivable.

After one to three weeks in each case, the explants are transferred to fresh medium until plumules and small shoots develop, which are then transferred to the same basal medium including timentin and PPT or alternative components with growth regulators, namely, for example, 0.5 mg/l indolylbutyric acid (IBA) and 0.5 mg/l gibberellic acid GA3, for rooting. Rooted shoots can be transferred into the glasshouse.

In addition to the method described, the following advantageous modifications are possible:

Before the explants are infected with the bacteria, they can be preincubated on the medium described above for the cocultivation for 1 to 12 days, preferably 3 to 4. This is followed by infection, cocultivation and selective regeneration as described above.

The pH for the regeneration (normally 5.8) can be lowered to pH 5.2. This improves control of the growth of *agrobacteria*.

Addition of $AgNO_3$ (3 to 10 mg/l) to the regeneration medium improves the condition of the culture, including the regeneration itself.

Components which reduce phenol formation and are known to the skilled worker, such as, for example citric acid, ascorbic acid, PVP and many others, have beneficial effects on the culture.

Liquid culture medium can also be used for the whole method. The culture can also be incubated on commercially available supports which are positioned on the liquid medium.

We claim:

1. A method for the targeted transgenic expression of nucleic acid sequences in nonreproductive floral tissues of plants, comprising the following steps,
   I. introducing a transgenic expression cassette into plant cells, wherein the transgenic expression cassette comprises at least the following elements
      a) at least one promoter sequence selected from a promoter sequence comprising the polynucleotide of SEQ ID NO: 1; or a promoter sequence comprising a fragment of SEQ ID NO: 1, wherein said fragment targets expression of a nucleic acid sequence in nonreproductive floral tissues of plants; and
      b) at least one further nucleic acid sequence,
   wherein the at least one promoter sequence and the at least one further nucleic acid sequence are functionally linked together, and the further nucleic acid sequence is heterologous in relation to the promoter sequence,
   II. selecting transgenic cells which comprise said expression cassette stably integrated into the genome, and
   III. regenerating complete plants from said transgenic cells, wherein the further nucleic acid sequence is expressed in nonreproductive floral tissues.

2. A transgenic expression cassette for the targeted transgenic expression of nucleic acid sequences in nonreproductive floral tissues of plants, comprising
   a) at least one promoter sequence selected from a promoter sequence comprising the polynucleotide of SEQ ID NO: 1; or
   a promoter sequence comprising a fragment of SEQ ID NO: 1, wherein said fragment targets expression of a nucleic acid sequence in nonreproductive floral tissues of plants; and
   b) at least one further nucleic acid sequence,
   wherein the at least one promoter sequence and the at least one further nucleic acid sequence are functionally linked together, and the further nucleic acid sequence is heterologous in relation to the promoter sequence, and wherein the promoter targets expression of the further nucleic acid sequence in nonreproductive floral tissues of plants.

3. The transgenic expression cassette according to claim 2, wherein
   a) the at least one further nucleic acid sequence is functionally linked with further genetic control sequences, or
   b) the expression cassette comprises additionally functional elements, or
   c) a) and b).

4. The transgenic expression cassette according to claim 2, wherein the further nucleic acid sequence a) encodes a protein, or
b) transcribes a sense-RNA, anti-sense RNA or double-stranded RNA.

5. The transgenic expression cassette according to claim 2, wherein the further nucleic acid sequence is selected from the group of nucleic acid sequences encoding chalcone synthases, phenylalanine ammonium lyases, photolyases, deoxyxylulose-5-phosphate synthases, phytoene synthases, phytoene desaturases, lycopene cyclases, hydroxylases, "antifreeze" polypeptides, CBF1-transcription activators, glutamate dehydrogenases, calcium-dependent protein kinases, calcineurin, farnesyltransferases, ferritin, oxalate oxidases, DREB1A factor, trehalose-phosphate phosphatases, chitinases, glucanases, ribosome-inactivating protein, lysozyme, *Bacillus thuringiensis* endotoxins, amylase inhibitors, protease inhibitors, lectins, RNAses, ribozymes, endochitinase, cytochrome P-450, acetyl-CoA carboxylases, amino acid transporters, monosaccharide-transporters, lycopine cyklases, carotene ketolases, endoxyloglucan transferases, Δ6-acyllipid desaturases, Δ6-desaturases, Δ5-fatty acid desaturases, Δ6-elongases and IPP-isomerases.

6. The trausgenic expression cassette according to claim 2, wherein the further nucleic acid sequence is selected from the group of nucleic acid sequences described by GenBank Accession Number: M20308, BAB00748, U62549, U77378, S78423, U32624, L25042, X92657, AJ002399, D45881, AF163819, AB044391, AJ222980 and AF078796.

7. A transgenic expression vector comprising the expression cassette according to claim 2.

8. A transgenic bacteria, plant, cells, cell cultures, parts, tissues, organs or propagation material obtained therefrom, transformed with the expression cassette of claim 2.

9. The transgenic plant as claimed in claim 8, wherein the plant is an agricultural crop plant.

10. The method of claim 1, wherein the transgenic expression cassette further comprises genetic control elements.

11. The trausgenic expression cassette of claim 2, wherein the expression cassette further comprises genetic control elements.

12. A transgenic bacteria, plant, cells, cell cultures, parts, tissues, organs or propagation material obtained therefrom, transformed with the vector of claim 10.

13. The method of claim 1, wherein the fragment of SEQ ID NO: 1 comprises nucleotides 1007 to 2039 of SEQ ID NO: 1.

14. The transgenic expression cassette of claim 2, wherein the fragment of SEQ ID NO: 1 comprises nucleotides 1007 to 2039 of SEQ ID NO: 1.

* * * * *

UNITED STATES PATENT AND TRADEMARK OFFICE
CERTIFICATE OF CORRECTION

| | | |
|---|---|---|
| PATENT NO. | : 7,402,733 B2 | Page 1 of 1 |
| APPLICATION NO. | : 10/526411 | |
| DATED | : July 22, 2008 | |
| INVENTOR(S) | : Martin Klebsattel et al. | |

It is certified that error appears in the above-identified patent and that said Letters Patent is hereby corrected as shown below:

In Claim 11, in column 68, on line 49, "11. The trausgenic expression cassette of claim 2, wherein" should read -- 11. The transgenic expression cassette of claim 2, wherein --.

Signed and Sealed this

Twenty-eighth Day of October, 2008

JON W. DUDAS
*Director of the United States Patent and Trademark Office*

SEQUENCE LISTING

```
<160> NUMBER OF SEQ ID NOS: 36

<210> SEQ ID NO 1
<211> LENGTH: 2039
<212> TYPE: DNA
<213> ORGANISM: Arabidopsis thaliana
<220> FEATURE:
<221> NAME/KEY: promoter
<222> LOCATION: (1)..(2039)
<223> OTHER INFORMATION: 76L promoter (including 5'-untranslated region)
      of gene locus At3g01980

<400> SEQUENCE: 1
tatcctctgc gcaatgaatt caacaaacgt tttacacaaa gaaaaaaacc tgttgaaaat         60
gaaagaaaaa aagtgatgaa atacattaga aacctttttgg atatagtcaa ggacttgagt       120
gtctctgatc ttattgccat cttggtcgat gactttgaaa acgtccatga accaacctcc       180
atcggaagag atgtaagctt tcttgatcac aagattcata tcagtgagca cttgtactac       240
ttccaataga gtcccatgtt tgttcacact atcaacctt tatttagcac cacaaacaaa        300
cagggaactc tgttttctca aaatctcttt gtttggtaca gaaccacttg aacaatttga       360
agagacagat ttatttacct gaataacagt ggcatcgtcg cttgcgttgt tgtctattac       420
aactctgtat ccaccatgaa acatacataa ataaagatga atgttttagc agctggaatc       480
tttacaaggg tatagaggct cacaaacgga gcatggagaa acagaggacc tagaaaacaa       540
taaaagagta tggagagaaa gagaaaaacc tgggaggatt cattctcctg atgagcttgg       600
catattcatc atcatccatg gttgtagtat gtatctcctt ggtgatttgg ctgcagcaga       660
aacccagaag agtgtgagtc ctccaatttc tgaggaaaat tcctaaaaga gagagggaga       720
gggaagttga aggaggataa aaatggtagg ccaccggaac cgaaccttgt tttcattagt       780
tgatcgagca cgtgccacta aagattctta gagatgacgt ggcacgggca cagcaacttt       840
tagattctgt tataattgtt cgaatactac caaaagtcgg gtgaagattt ggggtcaatt       900
tgatgatcat aaaggggatt atattctcct tctcaagcaa gatgtggtat ttactagtat       960
aatagatcat tcgttatctt gaggtagacc tctccgtaac gttcacaggt gcatgaccaa      1020
gtaacaattt gattcctttc cagcataacg tcatgttggt tgcaaaaaga aggcaaagta      1080
gagcaagcaa gcaagcaaag cattttttctt attttatatt ttgttgcgga ttccaccacc     1140
cacttgaaaa attgacatgt cacaatgatt tcgtatccta gtctttttatt atttaacact     1200 ctcacaatcc cattactcta cacctctttc attaagtcaa cacacggttt tcaaaaatcc      1260
actaccctcc caccacctag aatcttttgt tacctaccaa caccctcctt tgttctcttt     1320
atatattggt ccaactaaat caataaggga aagcatcctt ttggttggag gaattgcttt    1380
cattctcact ctttgtgtgt tgatcaatgg actagctaat aacaagttcc tcctctatat     1440
```

```
atttcaaaag aatggaacag aaacataaac gaaagacaga gtacctgatg ttgatgattc      1500
attgtctgtc tggagctccc aaatgccttt tatgcttaca tattcataac caacaacggc      1560
tattaattat aaaccaaaaa cacgaaataa gtttgtagca aagtgaaatt aggaatcttg      1620
gagatggatc cattagtagt aggataatag gatatgatgg aatttggttg gggaacagtg      1680
ataacttacg cttgcttccg gcgccgggaa agttggaaaa cctacaaagt acagaaatgg      1740
atctgggcct tgaagtgggc ttttattaa agaaaaaaat acatctccgt tatcaatcac       1800
catcttcttc tatctacaaa ttaaagaagg taacaacaga acgtggtgga tcatgtggtt      1860
aggcattaat tatttgcttt gtttcgccgt tttggtaaca cacagacaca gttccggtaa      1920
gagcttttgc agccactctt tatagttatt tagaattggc gatcgaatca atctcactcc      1980
ctccctccct taagtcttgt tgaatctgct gaattgtttt ataaagagtt actttggca       2039

<210> SEQ ID NO 2
<211> LENGTH: 2180
<212> TYPE: DNA
<213> ORGANISM: Arabidopsis thaliana
<220> FEATURE:
<221> NAME/KEY: promoter
<222> LOCATION: (1)..(2180)
<223> OTHER INFORMATION: 84L promoter (including 5'-untranslated region)
      of gene locus At1g63140

<400> SEQUENCE: 2
catgtttcag aggatatgtt cacaacaatt ccaaaagcag atgccatctt catgaaagta        60
aactcatata tatttcattc atggaaaagt ttaatcaata acaaatacta tcttcatttc       120
ataaaagcct tgtttcagat tttttcacac acatttaaaa gtgttttaag tttatcttat       180
acctttaagt acatttatga ttttttttt ctcctattaa ataagctgaa agattataga        240
taaatggttt tgtttatta aaaatgatgc attgaaaata taaaggaca ttttatatat         300 agatactaca tgattaggcc gatggaacca aagatgagcg actcttcttg taacattgtg       360
tttgctacgc aatgctcggt ttttttttc ttagatcgag actttgcctg agattctggt       420
tttcttcgat tgtgaaatca tatatgtctt gccttctcat ataggttcaa cattgaccaa       480
caaaaactac gggtggttta gttttttttg ggtggagagt ggagactaac cttgaccttt       540
ttcatttgta atgattttc tttcttgtat gaactattgt ttgtttattg gcgctgttca       600
tttgttccga gtgttttcgt atatgcttta acaagcacg tactatcagc aatagcaaaa       660
gtaacatgat atttgttaat cccgttggaa attcatgtcc attattttgt atatatatat       720
attatataat agtagaattt ggttatgtag tgcatattct ctaaatctat gctttctaag       780
gttaaaaaca ggcgcccata tggacgacat aaatgtcgat atttaagagg cactgcaagt       840
tgaacaaaaa aaaaaagta taggcactgc aaaagttatc caacgtattt aagactaagg       900 actaagatt caaagataat attcagaaaa agaaaaagaa aaaagagaa gataatattc         960 ggaaacatcc acaagcattc taaatctaga aacataaat aatacagcaa agatggggat       1020
gaagatatga tccaactcca tcacagattc tcaagacaga tttagaaagt gtcaagctca      1080 ccaaagggt tataggagac tgactgttaa ttgaaatgct ttctacacgt ggacgcactg        1140
atatcatatt aaaacctgat tgtttgttga acattcacta actcatacca aacggtccaa      1200
acctatgtct ccatttttctt aaatgttgat ttcgattcca tacctacttt gcatacatta    1260
ttgaatgtgt tccttaagtt gtgattaaaa ttaaatgagc acaatatcac agtcgaatgg      1320
tatatcgatg taacactta ggattgaatc aatatgaaaa gttatacacc gaatttgtga       1380
```

```
gaaacgagta tagcttagac aaaatttgtt tttcttaaat taagcggaaa aataattaaa   1440
cagagaccaa attaagcgtt cttcttgaac tgaaatcact aaagtaaagt taacccgtta   1500
gtagagtgtt aactatttaa acaaagaaaa ctccaaaccc aattgagaaa ctactcaaac   1560
atagaaacaa cacataatga ttcagtagct accaatatca tattcaactt tgtttcgatt   1620
cctttaaaac aaaatataat taaccaaata aaataggtca taatcgattc agaaacaatt   1680
tcatattctt ctctagttta gttcagtttc attctaccgg agttgtatac aatctataat   1740
tttatcgctt attccttaa aagcgtcctc aaaccaacca aaacaaaaat agttgcatca    1800
atgaatccat caaagcatat aaattcacac cgtcttaaaa tggagtgttg atggataagt   1860
accaacaatt ttagaccatt cacactgaat gagtatgact aacattcaca ttcacattca   1920
attaggaaag ttgtactaat gaacacacaa taaaagtgaa acaaatctc tacatattct   1980 tgtacaccaa tctatattag atgatcattt taaatataca cgaatattaa ttttataaat   2040
gaaaaatacg tgcccatatt ttaattaatt tatatattta gctatcaaat attaggcata   2100
atgttggtga ggtttctgag tataaaaaat gacaaagtat gaataccatc tatacccttta  2160 ttacctatct ttctcgattt                                                2180

<210> SEQ ID NO 3
<211> LENGTH: 1033
<212> TYPE: DNA
<213> ORGANISM: Arabidopsis thaliana
<220> FEATURE:
<221> NAME/KEY: promoter
<222> LOCATION: (1)..(1033)
<223> OTHER INFORMATION: 76S promoter (including 5'-untranslated region)
      of gene locus At3g01980

<400> SEQUENCE: 3
aggtgcatga ccaagtaaca atttgattcc tttccagcat aacgtcatgt tggttgcaaa     60
aagaaggcaa agtagagcaa gcaagcaagc aaagcatttt tcttatttta tattttgttg   120
cggattccac cacccacttg aaaaattgac atgtcacaat gatttcgtat cctagtcttt    180
tattatttaa cactctcaca atcccattac tctacacctc tttcattaag tcaacacacg   240
gttttcaaaa atccactacc ctcccaccac ctagaatctt ttgttaccta ccaacacccct   300 cctttgttct ctttatatat tggtccaact aaatcaataa gggaaagcat cctttttggtt   360 ggaggaattg ctttcattct cactctttgt gtgttgatca atggactagc taataacaag   420
ttcctcctct atatatttca aaagaatgga acagaaacat aaacgaaaga cagagtacct   480
gatgttgatg attcattgtc tgtctggagc tcccaaatgc cttttatgct tacatattca   540
taaccaacaa cggctattaa ttataaacca aaaacacgaa ataagtttgt agcaaagtga    600
aattaggaat cttggagatg gatccattag tagtaggata ataggatatg atggaatttg   660 gttgggggaac agtgataact tacgcttgct tccggcgccg ggaaagttgg aaaacctaca   720
aagtacagaa atggatctgg gccttgaagt gggcttttta ttaaagaaaa aaatacatct    780
ccgttatcaa tcaccatctt cttctatcta caaattaaag aaggtaacaa cagaacgtgg    840
tggatcatgt ggttaggcat taattatttg ctttgtttcg ccgttttggt aacacacaga    900
cacagttccg gtaagagctt ttgcagccac tctttatagt tatttagaat tggcgatcga    960
atcaatctca ctccctccct cccttaagtc ttgttgaatc tgctgaattg ttttataaag   1020
agttactttg gca                                                      1033
```

```
<210> SEQ ID NO 4
<211> LENGTH: 1097
<212> TYPE: DNA
<213> ORGANISM: Arabidopsis thaliana
<220> FEATURE:
<221> NAME/KEY: promoter
<222> LOCATION: (1)..(1097)
<223> OTHER INFORMATION: 84S promoter (including 5'-untranslated region)
      of gene locus At1g63140

<400> SEQUENCE: 4
aaagggttat aggagactga ctgttaattg aaatgctttc tacacgtgga cgcactgata      60
tcatattaaa acctgattgt ttgttgaaca ttcactaact cataccaaac ggtccaaacc     120
tatgtctcca ttttcttaaa tgttgatttc gattccatac ctactttgca tacattattg     180
aatgtgtttc ttaagttgtg attaaaatta aatgagcaca atatcacagt cgaatggtat     240
atcgatgtaa cactttagga ttgaatcaat atgaaaagtt atacaccgaa tttgtgagaa     300
acgagtatag cttagacaaa atttgttttt cttaaattaa gcggaaaaat aattaaacag     360
agaccaaatt aagcgttctt cttgaactga atcactaaa gtaaagttaa cccgttagta      420
gagtgttaac tatttaaaca aagaaaactc caaacccaat tgagaaacta ctcaaacata     480
gaaacaacac ataatgattc agtagctacc aatatcatat tcaactttgt ttcgattcct     540
ttaaaacaaa atataattaa ccaaataaaa taggtcataa tcgattcaga aacaatttca     600
tattcttctc tagtttagtt cagtttcatt ctaccggagt tgtatacaat ctataatttt     660
atcgcttatt accttaaaag cgtcctcaaa ccaaccaaaa caaaaatagt tgcatcaatg     720
aatccatcaa agcatataaa ttcacaccgt cttaaaatgg agtgttgatg gataagtacc     780
aacaatttta gaccattcac actgaatgag tatgactaac attcacattc acattcaatt     840
aggaaagttg tactaatgaa cacacaataa aagtgaaaac aaatctctac atattcttgt     900
acaccaatct atattagatg atcattttaa atatacacga atattaattt tataaatgaa     960
aaatacgtgc ccatatttta attaatttat atatttagct atcaaatatt aggcataatg    1020
ttggtgaggt ttctgagtat aaaaaatgac aaagtatgaa taccatctat acctttatta    1080
cctatctttc tcgattt                                                   1097

<210> SEQ ID NO 5
<211> LENGTH: 19
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 5
gaccctgtcc cacctccaa                                                   19

<210> SEQ ID NO 6
<211> LENGTH: 21
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 6
tgagaactgc gattgtttgc a                                                21

<210> SEQ ID NO 7
<211> LENGTH: 25
```

-continued

```
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 7
gtcgactatc ctctgcgcaa tgaat                                              25

<210> SEQ ID NO 8
<211> LENGTH: 25
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 8
cccgggaaat cgagaaagat aggta                                              25

<210> SEQ ID NO 9
<211> LENGTH: 25
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 9
gtcgacaaag ggttatagga gactg                                              25

<210> SEQ ID NO 10
<211> LENGTH: 25
<212> TYPE: DNA
<213> ORGANISM: Artificial sequence
<220> FEATURE:
<223> OTHER INFORMATION: Description of the artificial sequence:
      Oligonucleotide primer

<400> SEQUENCE: 10
gtcgaccatg tttcagagga tatgt                                              25

<210> SEQ ID NO 11
<211> LENGTH: 1187
<212> TYPE: DNA
<213> ORGANISM: Arabidopsis thaliana
<220> FEATURE:
<221> NAME/KEY: CDS
<222> LOCATION: (132)..(764)
<223> OTHER INFORMATION: coding   for gene product of  Arabidopsis
      thaliana gene locus At3g01980

<400> SEQUENCE: 11
gttccggtaa gagcttttgc agccactctt tatagttatt tagaattggc gatcgaatca         60
atctcactcc ctccctccct aagtcttgt tgaatctgct gaattgtttt ataaagagtt        120
actttggcaa a atg gaa aat ccg gcg aag aga gtg ttg atg aca tcc aac        170
            Met Glu Asn Pro Ala Lys Arg Val Leu Met Thr Ser Asn
              1               5                  10 ggc gac gag gtg tcc cga aac atc gct ttc cat cta gcc aaa cac ggt        218
Gly Asp Glu Val Ser Arg Asn Ile Ala Phe His Leu Ala Lys His Gly
         15                  20                  25 tgc aag ttg gta atg atg gga aat gag ggt tcc cta agg agc att gta        266
Cys Lys Leu Val Met Met Gly Asn Glu Gly Ser Leu Arg Ser Ile Val
 30                  35                  40                  45 gac aag att aga gat tcc att gag gga gcc ttc cct gcc gat gtt ata        314
```

-continued

```
                Asp Lys Ile Arg Asp Ser Ile Glu Gly Ala Phe Pro Ala Asp Val Ile
                             50                  55                  60 gca ctc gac atg gaa tct gac tct gaa gtt gct ttt cat gcc gct gtc          362
Ala Leu Asp Met Glu Ser Asp Ser Glu Val Ala Phe His Ala Ala Val
             65                  70                  75 caa aag gca tgg gaa ctt tcc ggc cat ttc gat gct ttt ctc aac tct          410
Gln Lys Ala Trp Glu Leu Ser Gly His Phe Asp Ala Phe Leu Asn Ser
         80                  85                  90 tat acc tac caa ggt tta att tgc ttc ttg ttt ttc act acc ctg cct          458
Tyr Thr Tyr Gln Gly Leu Ile Cys Phe Leu Phe Phe Thr Thr Leu Pro
         95                 100                 105 ttg atg ctc ttg tgt gtt gat cat tcc ttt att caa caa tct ttc ttt          506
Leu Met Leu Leu Cys Val Asp His Ser Phe Ile Gln Gln Ser Phe Phe
110                 115                 120                 125 ctt gca gga aag gtg cag gac att ctt caa gtc tct caa gat gag ttc          554
Leu Ala Gly Lys Val Gln Asp Ile Leu Gln Val Ser Gln Asp Glu Phe
             130                 135                 140 cac aga atc aca aag atc aat ctc acc gct cca tgg ttt ctc ttg aag          602
His Arg Ile Thr Lys Ile Asn Leu Thr Ala Pro Trp Phe Leu Leu Lys
             145                 150                 155 gct gta gcc aca agg atg aag gac cat gga tca gga ggc tcc att gtc          650
Ala Val Ala Thr Arg Met Lys Asp His Gly Ser Gly Gly Ser Ile Val
         160                 165                 170 ttc atg gcc act atc gcc agc gga gag agg gcg ctt tac cct ggc gct          698
Phe Met Ala Thr Ile Ala Ser Gly Glu Arg Ala Leu Tyr Pro Gly Ala
    175                 180                 185 gat gcc tac gct tca act tct gcc gct att cac cag ctc gtc cgg gta          746
Asp Ala Tyr Ala Ser Thr Ser Ala Ala Ile His Gln Leu Val Arg Val
190                 195                 200                 205 tgc atc cta gct cct aat tagacacatc gcgttcgtaa cttgaatatg                  794
Cys Ile Leu Ala Pro Asn
             210 tttgttgatg attgggtttc aggcatcagc catgagtctc gggaagcaca agatacgggt         854 caacatgatc tctagagggc tgcatctgga tgatgagtat acagcttctg tgggaagaga         914 ccgagcgcag aagctggtca aggacgctgc accccctcggc cagtggctca acccggacac        974 agacctctac tccactgtta tctacttgat cagcgatggc tcacgcttca tgacaggcac       1034 cactgtcttg gtggatggag cgcagtccct tacgcgaccc cgtctcaaat cctacatgtg       1094 atcaatgcct agtattatta taattctatg ttgtgtgtaa aaagtgaata tgaatcaagt       1154 ttgaataact atggagggat gaataatcca tcc                                    1187

<210> SEQ ID NO 12
<211> LENGTH: 211
<212> TYPE: PRT
<213> ORGANISM: Arabidopsis thaliana

<400> SEQUENCE: 12

Met Glu Asn Pro Ala Lys Arg Val Leu Met Thr Ser Asn Gly Asp Glu
1               5                  10                  15

Val Ser Arg Asn Ile Ala Phe His Leu Ala Lys His Gly Cys Lys Leu
             20                  25                  30

Val Met Met Gly Asn Glu Gly Ser Leu Arg Ser Ile Val Asp Lys Ile
         35                  40                  45

Arg Asp Ser Ile Glu Gly Ala Phe Pro Ala Asp Val Ile Ala Leu Asp
     50                  55                  60

Met Glu Ser Asp Ser Glu Val Ala Phe His Ala Ala Val Gln Lys Ala
65                  70                  75                  80
```

-continued

```
Trp Glu Leu Ser Gly His Phe Asp Ala Phe Leu Asn Ser Tyr Thr Tyr
             85                  90                  95

Gln Gly Leu Ile Cys Phe Leu Phe Thr Thr Leu Pro Leu Met Leu
        100                 105                 110

Leu Cys Val Asp His Ser Phe Ile Gln Gln Ser Phe Phe Leu Ala Gly
        115                 120                 125

Lys Val Gln Asp Ile Leu Gln Val Ser Gln Asp Glu Phe His Arg Ile
130                 135                 140

Thr Lys Ile Asn Leu Thr Ala Pro Trp Phe Leu Leu Lys Ala Val Ala
145                 150                 155                 160

Thr Arg Met Lys Asp His Gly Ser Gly Gly Ser Ile Val Phe Met Ala
                165                 170                 175

Thr Ile Ala Ser Gly Glu Arg Ala Leu Tyr Pro Gly Ala Asp Ala Tyr
            180                 185                 190

Ala Ser Thr Ser Ala Ala Ile His Gln Leu Val Arg Val Cys Ile Leu
        195                 200                 205

Ala Pro Asn
    210
```

<210> SEQ ID NO 13
<211> LENGTH: 1146
<212> TYPE: DNA
<213> ORGANISM: Arabidopsis thaliana
<220> FEATURE:
<221> NAME/KEY: CDS
<222> LOCATION: (1)..(1143)
<223> OTHER INFORMATION: coding for transcript (cDNA) of gene locus At1g63140

<400> SEQUENCE: 13

```
atg gag aac cat ctt caa cat tcc tta acc atc att cct aaa ccg gat      48
Met Glu Asn His Leu Gln His Ser Leu Thr Ile Ile Pro Lys Pro Asp
 1               5                  10                  15 cta atc aaa gaa gaa caa cgt tat cac gaa gat acg gtg agc ttg caa      96
Leu Ile Lys Glu Glu Gln Arg Tyr His Glu Asp Thr Val Ser Leu Gln
             20                  25                  30 gcg gag agg att ttg cat gcc atg acc ttc ccc atg gtt ctc aaa act     144
Ala Glu Arg Ile Leu His Ala Met Thr Phe Pro Met Val Leu Lys Thr
         35                  40                  45 gct ttg gag ctt ggc gtt atc gac atg atc act tct gta gat gac ggc     192
Ala Leu Glu Leu Gly Val Ile Asp Met Ile Thr Ser Val Asp Asp Gly
     50                  55                  60 gtg tgg ctc tcg cct tct gag atc gct ctt ggt ctc cca acc aag ccc     240
Val Trp Leu Ser Pro Ser Glu Ile Ala Leu Gly Leu Pro Thr Lys Pro
 65                  70                  75                  80 acc aat ccg gag gca cca gta ttg ctg gac cgg atg cta gtt ttg tta     288
Thr Asn Pro Glu Ala Pro Val Leu Leu Asp Arg Met Leu Val Leu Leu
                 85                  90                  95 gcc agc cac tca atc ttg aag tac cgt acg gta gaa acc gga gat aac     336
Ala Ser His Ser Ile Leu Lys Tyr Arg Thr Val Glu Thr Gly Asp Asn
            100                 105                 110 att gga agt aga aag acc gag agg gtc tat gca gct gaa ccg gtt tgc     384
Ile Gly Ser Arg Lys Thr Glu Arg Val Tyr Ala Ala Glu Pro Val Cys
        115                 120                 125 acg ttt ttc ttg aac cgc gga gat ggc ttg ggc tct ctc gcc act ttg     432
Thr Phe Phe Leu Asn Arg Gly Asp Gly Leu Gly Ser Leu Ala Thr Leu
    130                 135                 140 ttc atg gta ctc caa ggg gaa gtc tgt atg aag cct tgg gaa cat ctc     480
Phe Met Val Leu Gln Gly Glu Val Cys Met Lys Pro Trp Glu His Leu
```

```
                    145                 150                 155                 160
aaa gac atg ata tta gaa gga aaa gat gca ttc acc tct gct cat ggc           528
Lys Asp Met Ile Leu Glu Gly Lys Asp Ala Phe Thr Ser Ala His Gly
                165                 170                 175 atg agg ttt ttc gaa ctc att ggt tcg aac gaa caa ttc gct gaa atg           576
Met Arg Phe Phe Glu Leu Ile Gly Ser Asn Glu Gln Phe Ala Glu Met
            180                 185                 190 ttt aac cgg gca atg tcg gaa gct tcc aca ttg att atg aag aag gtt           624
Phe Asn Arg Ala Met Ser Glu Ala Ser Thr Leu Ile Met Lys Lys Val
        195                 200                 205 tta gaa gtt tac aaa gga ttc gaa gat gta aat act ttg gtg gat gtg           672
Leu Glu Val Tyr Lys Gly Phe Glu Asp Val Asn Thr Leu Val Asp Val
    210                 215                 220 gga gga gga att gga aca atc ata ggt caa gtg act tcc aag tat cct           720
Gly Gly Gly Ile Gly Thr Ile Ile Gly Gln Val Thr Ser Lys Tyr Pro
225                 230                 235                 240 cat att aaa ggc atc aat ttc gat cta gca tcg gtt tta gcc cat gct           768
His Ile Lys Gly Ile Asn Phe Asp Leu Ala Ser Val Leu Ala His Ala
                245                 250                 255 cct ttt aat aaa gga gtg gag cat gtt tca gga gat atg ttt aaa gaa           816
Pro Phe Asn Lys Gly Val Glu His Val Ser Gly Asp Met Phe Lys Glu
            260                 265                 270 att cca aaa gga gat gcc atc ttc atg aaa tgg ata cta cat gat tgg           864
Ile Pro Lys Gly Asp Ala Ile Phe Met Lys Trp Ile Leu His Asp Trp
        275                 280                 285 act gac gaa gat tgt gta aag atc cta aaa aat tat tgg aaa agt ctt           912
Thr Asp Glu Asp Cys Val Lys Ile Leu Lys Asn Tyr Trp Lys Ser Leu
    290                 295                 300 ccc gag aaa gga aaa gtg ata ata gtc gag gtg gtt acg ccc gag gaa           960
Pro Glu Lys Gly Lys Val Ile Ile Val Glu Val Val Thr Pro Glu Glu
305                 310                 315                 320 cca aag att aac gac att tct tct aac att gtg ttc ggt atg gac atg          1008
Pro Lys Ile Asn Asp Ile Ser Ser Asn Ile Val Phe Gly Met Asp Met
                325                 330                 335 ctg atg tta gca gta agc tca ggt ggt aag gag agg tct ctt tcc caa          1056
Leu Met Leu Ala Val Ser Ser Gly Gly Lys Glu Arg Ser Leu Ser Gln
            340                 345                 350 ttc gag act cta gcc tct gat tcg ggt ttt ctt cgt tgt gaa atc att          1104
Phe Glu Thr Leu Ala Ser Asp Ser Gly Phe Leu Arg Cys Glu Ile Ile
        355                 360                 365 tgt cat gcc ttc tca tat agt gtt atc gaa tta cac aaa tag                  1146
Cys His Ala Phe Ser Tyr Ser Val Ile Glu Leu His Lys
    370                 375                 380

<210> SEQ ID NO 14
<211> LENGTH: 381
<212> TYPE: PRT
<213> ORGANISM: Arabidopsis thaliana

<400> SEQUENCE: 14

Met Glu Asn His Leu Gln His Ser Leu Thr Ile Ile Pro Lys Pro Asp
 1                5                  10                 15

Leu Ile Lys Glu Glu Gln Arg Tyr His Glu Asp Thr Val Ser Leu Gln
            20                  25                 30

Ala Glu Arg Ile Leu His Ala Met Thr Phe Pro Met Val Leu Lys Thr
        35                  40                 45

Ala Leu Glu Leu Gly Val Ile Asp Met Ile Thr Ser Val Asp Asp Gly
    50                  55                 60

Val Trp Leu Ser Pro Ser Glu Ile Ala Leu Gly Leu Pro Thr Lys Pro
```

```
                65                  70                  75                  80
Thr Asn Pro Glu Ala Pro Val Leu Leu Asp Arg Met Leu Val Leu Leu
                    85                  90                  95
Ala Ser His Ser Ile Leu Lys Tyr Arg Thr Val Glu Thr Gly Asp Asn
                100                 105                 110
Ile Gly Ser Arg Lys Thr Glu Arg Val Tyr Ala Ala Glu Pro Val Cys
                115                 120                 125
Thr Phe Phe Leu Asn Arg Gly Asp Gly Leu Gly Ser Leu Ala Thr Leu
    130                 135                 140
Phe Met Val Leu Gln Gly Glu Val Cys Met Lys Pro Trp Glu His Leu
145                 150                 155                 160
Lys Asp Met Ile Leu Glu Gly Lys Asp Ala Phe Thr Ser Ala His Gly
                165                 170                 175
Met Arg Phe Phe Glu Leu Ile Gly Ser Asn Glu Gln Phe Ala Glu Met
                180                 185                 190
Phe Asn Arg Ala Met Ser Glu Ala Ser Thr Leu Ile Met Lys Lys Val
                195                 200                 205
Leu Glu Val Tyr Lys Gly Phe Glu Asp Val Asn Thr Leu Val Asp Val
    210                 215                 220
Gly Gly Gly Ile Gly Thr Ile Gly Gln Val Thr Ser Lys Tyr Pro
225                 230                 235                 240
His Ile Lys Gly Ile Asn Phe Asp Leu Ala Ser Val Leu Ala His Ala
                245                 250                 255
Pro Phe Asn Lys Gly Val Glu His Val Ser Gly Asp Met Phe Lys Glu
                260                 265                 270
Ile Pro Lys Gly Asp Ala Ile Phe Met Lys Trp Ile Leu His Asp Trp
                275                 280                 285
Thr Asp Glu Asp Cys Val Lys Ile Leu Lys Asn Tyr Trp Lys Ser Leu
    290                 295                 300
Pro Glu Lys Gly Lys Val Ile Ile Val Glu Val Val Thr Pro Glu Glu
305                 310                 315                 320
Pro Lys Ile Asn Asp Ile Ser Ser Asn Ile Val Phe Gly Met Asp Met
                325                 330                 335
Leu Met Leu Ala Val Ser Ser Gly Gly Lys Glu Arg Ser Leu Ser Gln
                340                 345                 350
Phe Glu Thr Leu Ala Ser Asp Ser Gly Phe Leu Arg Cys Glu Ile Ile
                355                 360                 365
Cys His Ala Phe Ser Tyr Ser Val Ile Glu Leu His Lys
    370                 375                 380

<210> SEQ ID NO 15
<211> LENGTH: 394
<212> TYPE: DNA
<213> ORGANISM: Brassica napus
<220> FEATURE:
<221> NAME/KEY: CDS
<222> LOCATION: (3)..(392)
<223> OTHER INFORMATION: coding for Brassica homologue H2

<400> SEQUENCE: 15 cc aac ggc gac gag gtt tcc cgg aac atc gct atc caa cta gcc aaa        47
   Asn Gly Asp Glu Val Ser Arg Asn Ile Ala Ile Gln Leu Ala Lys
    1               5                  10                  15 cac ggt tgt cgg ttg gtg ttg atg gga aac gag gct tct cta agg agc        95
His Gly Cys Arg Leu Val Leu Met Gly Asn Glu Ala Ser Leu Arg Ser
                20                  25                  30
```

```
act gtg gac tac ata cga gtc tct gtt gat gga gcc ttc cca gtg gag    143
Thr Val Asp Tyr Ile Arg Val Ser Val Asp Gly Ala Phe Pro Val Glu
         35                  40                  45 ctc att gga gcc gac atg gaa gct gat agt gag gaa gat ttc tat gtt    191
Leu Ile Gly Ala Asp Met Glu Ala Asp Ser Glu Glu Asp Phe Tyr Val
 50                  55                  60 gct gtc caa aag gca tgg act cgt cta gga tct ttg gat gct ttt gtc    239
Ala Val Gln Lys Ala Trp Thr Arg Leu Gly Ser Leu Asp Ala Phe Val
 65                  70                  75 aac tgc tgt acc tac caa ggg aag atg cag gac att ctc cga gtg tct    287
Asn Cys Cys Thr Tyr Gln Gly Lys Met Gln Asp Ile Leu Arg Val Ser
 80                  85                  90                  95 gaa gat gag ttc aag aaa atc aca agg atc aat ctc acg gct aca tgg    335
Glu Asp Glu Phe Lys Lys Ile Thr Arg Ile Asn Leu Thr Ala Thr Trp
                100                 105                 110 ttt atc ttg aag gct gtg gca agc atg atg aag gag aat gga aca gga    383
Phe Ile Leu Lys Ala Val Ala Ser Met Met Lys Glu Asn Gly Thr Gly
                115                 120                 125 ggc tcc att gg                                                     394
Gly Ser Ile
        130

<210> SEQ ID NO 16
<211> LENGTH: 130
<212> TYPE: PRT
<213> ORGANISM: Brassica napus

<400> SEQUENCE: 16

Asn Gly Asp Glu Val Ser Arg Asn Ile Ala Ile Gln Leu Ala Lys His
 1               5                  10                  15

Gly Cys Arg Leu Val Leu Met Gly Asn Glu Ala Ser Leu Arg Ser Thr
             20                  25                  30

Val Asp Tyr Ile Arg Val Ser Val Asp Gly Ala Phe Pro Val Glu Leu
         35                  40                  45

Ile Gly Ala Asp Met Glu Ala Asp Ser Glu Glu Asp Phe Tyr Val Ala
 50                  55                  60

Val Gln Lys Ala Trp Thr Arg Leu Gly Ser Leu Asp Ala Phe Val Asn
 65                  70                  75                  80

Cys Cys Thr Tyr Gln Gly Lys Met Gln Asp Ile Leu Arg Val Ser Glu
             85                  90                  95

Asp Glu Phe Lys Lys Ile Thr Arg Ile Asn Leu Thr Ala Thr Trp Phe
            100                 105                 110

Ile Leu Lys Ala Val Ala Ser Met Met Lys Glu Asn Gly Thr Gly Gly
            115                 120                 125

Ser Ile
    130

<210> SEQ ID NO 17
<211> LENGTH: 429
<212> TYPE: DNA
<213> ORGANISM: Brassica napus
<220> FEATURE:
<221> NAME/KEY: CDS
<222> LOCATION: (2)..(427)
<223> OTHER INFORMATION: coding for Brassica homologue H3

<400> SEQUENCE: 17 g gaa ttt tcg ggt cga cga ttt cgt act act ctg aat cta atg gcc aat    49
  Glu Phe Ser Gly Arg Arg Phe Arg Thr Thr Leu Asn Leu Met Ala Asn
   1               5                  10                  15
```

```
aag gtg ttg atg aca gac aac ggc gac cag gtt tcc cgg aac atc gct       97
Lys Val Leu Met Thr Asp Asn Gly Asp Gln Val Ser Arg Asn Ile Ala
             20                  25                  30 atc caa cta gcc aaa cac ggt tgt cgg ttg gtg ttg atg gga aac gag      145
Ile Gln Leu Ala Lys His Gly Cys Arg Leu Val Leu Met Gly Asn Glu
         35                  40                  45 gct tct cta agg agc act gtg gac tac ata cga ttc tct gat gat gga      193
Ala Ser Leu Arg Ser Thr Val Asp Tyr Ile Arg Phe Ser Asp Asp Gly
     50                  55                  60 gcc ttc cca gtg gag ctc att gga gcc gac atg gaa gct gat agt gag      241
Ala Phe Pro Val Glu Leu Ile Gly Ala Asp Met Glu Ala Asp Ser Glu
 65                  70                  75                  80 gaa gat ttc tat gtt gct gtc caa acg gca tgg act cgt cta gga tct      289
Glu Asp Phe Tyr Val Ala Val Gln Thr Ala Trp Thr Arg Leu Gly Ser
                 85                  90                  95 ttg gat gct ttt gtc aac tgc tgt acc tac caa ggg aag atg cag gac      337
Leu Asp Ala Phe Val Asn Cys Cys Thr Tyr Gln Gly Lys Met Gln Asp
            100                 105                 110 att ctc cga gtg tct gaa gat gag ttc aag aaa atc aca cgg atc aat      385
Ile Leu Arg Val Ser Glu Asp Glu Phe Lys Lys Ile Thr Arg Ile Asn
        115                 120                 125 ctc acg gct aca tgg ttt atc ttg aag gct gtg gca agc atg at           429
Leu Thr Ala Thr Trp Phe Ile Leu Lys Ala Val Ala Ser Met
    130                 135                 140

<210> SEQ ID NO 18
<211> LENGTH: 142
<212> TYPE: PRT
<213> ORGANISM: Brassica napus

<400> SEQUENCE: 18

Glu Phe Ser Gly Arg Arg Phe Arg Thr Thr Leu Asn Leu Met Ala Asn
 1               5                  10                  15

Lys Val Leu Met Thr Asp Asn Gly Asp Gln Val Ser Arg Asn Ile Ala
             20                  25                  30

Ile Gln Leu Ala Lys His Gly Cys Arg Leu Val Leu Met Gly Asn Glu
         35                  40                  45

Ala Ser Leu Arg Ser Thr Val Asp Tyr Ile Arg Phe Ser Asp Asp Gly
     50                  55                  60

Ala Phe Pro Val Glu Leu Ile Gly Ala Asp Met Glu Ala Asp Ser Glu
 65                  70                  75                  80

Glu Asp Phe Tyr Val Ala Val Gln Thr Ala Trp Thr Arg Leu Gly Ser
                 85                  90                  95

Leu Asp Ala Phe Val Asn Cys Cys Thr Tyr Gln Gly Lys Met Gln Asp
            100                 105                 110

Ile Leu Arg Val Ser Glu Asp Glu Phe Lys Lys Ile Thr Arg Ile Asn
        115                 120                 125

Leu Thr Ala Thr Trp Phe Ile Leu Lys Ala Val Ala Ser Met
    130                 135                 140

<210> SEQ ID NO 19
<211> LENGTH: 436
<212> TYPE: DNA
<213> ORGANISM: Brassica napus
<220> FEATURE:
<221> NAME/KEY: CDS
<222> LOCATION: (3)..(419)
<223> OTHER INFORMATION: coding for Brassica homologue H4

<400> SEQUENCE: 19
```

```
gt cga cga ttt cgt gga gaa aac aat cta act gga aag atc caa atg      47
   Arg Arg Phe Arg Gly Glu Asn Asn Leu Thr Gly Lys Ile Gln Met
    1               5                  10                  15 gta tat gca gcc gag ccg gtt tgc acg ctt ttc tta aaa cat ggt cat      95
Val Tyr Ala Ala Glu Pro Val Cys Thr Leu Phe Leu Lys His Gly His
                20                  25                  30 gag tcg ggt tca ctc atg tcc cta ttc atg gtg cac cat agc caa gtc     143
Glu Ser Gly Ser Leu Met Ser Leu Phe Met Val His His Ser Gln Val
            35                  40                  45 ttt ttc gaa act tgg aca cat ttg aaa gat ctg ata caa gaa gga aaa     191
Phe Phe Glu Thr Trp Thr His Leu Lys Asp Leu Ile Gln Glu Gly Lys
        50                  55                  60 gat aca ttc att tct gct cat ggc atg agg atc ttt gaa tac atc ggt     239
Asp Thr Phe Ile Ser Ala His Gly Met Arg Ile Phe Glu Tyr Ile Gly
    65                  70                  75 ttg aat gaa caa ttc gct tgt atg ttt aac cat gca atg tca gaa tct     287
Leu Asn Glu Gln Phe Ala Cys Met Phe Asn His Ala Met Ser Glu Ser
80                  85                  90                  95 tct acc atg atc atg aag aag att tta gaa gtt tac aga gga ttc gaa     335
Ser Thr Met Ile Met Lys Lys Ile Leu Glu Val Tyr Arg Gly Phe Glu
                100                 105                 110 gat att aaa act ttg gtg gat att gga gga gga ctt ggc acc aca cta     383
Asp Ile Lys Thr Leu Val Asp Ile Gly Gly Gly Leu Gly Thr Thr Leu
            115                 120                 125 aat ctg gtt act tcc aag tat cct cat ata agg gta taatttcgat          429
Asn Leu Val Thr Ser Lys Tyr Pro His Ile Arg Val
        130                 135 taaactc                                                              436

<210> SEQ ID NO 20
<211> LENGTH: 139
<212> TYPE: PRT
<213> ORGANISM: Brassica napus

<400> SEQUENCE: 20

Arg Arg Phe Arg Gly Glu Asn Asn Leu Thr Gly Lys Ile Gln Met Val
 1               5                  10                  15

Tyr Ala Ala Glu Pro Val Cys Thr Leu Phe Leu Lys His Gly His Glu
            20                  25                  30

Ser Gly Ser Leu Met Ser Leu Phe Met Val His His Ser Gln Val Phe
        35                  40                  45

Phe Glu Thr Trp Thr His Leu Lys Asp Leu Ile Gln Glu Gly Lys Asp
    50                  55                  60

Thr Phe Ile Ser Ala His Gly Met Arg Ile Phe Glu Tyr Ile Gly Leu
65                  70                  75                  80

Asn Glu Gln Phe Ala Cys Met Phe Asn His Ala Met Ser Glu Ser Ser
                85                  90                  95

Thr Met Ile Met Lys Lys Ile Leu Glu Val Tyr Arg Gly Phe Glu Asp
            100                 105                 110

Ile Lys Thr Leu Val Asp Ile Gly Gly Gly Leu Gly Thr Thr Leu Asn
        115                 120                 125

Leu Val Thr Ser Lys Tyr Pro His Ile Arg Val
    130                 135

<210> SEQ ID NO 21
<211> LENGTH: 418
<212> TYPE: DNA
<213> ORGANISM: Brassica napus
<220> FEATURE:
```

<221> NAME/KEY: CDS
<222> LOCATION: (1)..(417)
<223> OTHER INFORMATION: coding for Brassica homologue H5

<400> SEQUENCE: 21

```
gct gaa ccg gtt tgc acg ctt ttt tta acc cgt ggt gac gac tcg ggt     48
Ala Glu Pro Val Cys Thr Leu Phe Leu Thr Arg Gly Asp Asp Ser Gly
 1               5                  10                  15 act cac aag tcc ctc ttc atg ttg ctc aat agc caa gta ttt ttc aag     96
Thr His Lys Ser Leu Phe Met Leu Leu Asn Ser Gln Val Phe Phe Lys
             20                  25                  30 aca tgg gat aat ctg aag ggt gtg ata caa gaa gga aaa gat gcg ttt    144
Thr Trp Asp Asn Leu Lys Gly Val Ile Gln Glu Gly Lys Asp Ala Phe
         35                  40                  45 agt tca gct cat ggc atg cca tta ttc gaa tac atc ggt ttg gat gag    192
Ser Ser Ala His Gly Met Pro Leu Phe Glu Tyr Ile Gly Leu Asp Glu
     50                  55                  60 caa ttc gct ggt atg ttt aac cat gca atg gca gaa tct tct acc atc    240
Gln Phe Ala Gly Met Phe Asn His Ala Met Ala Glu Ser Ser Thr Ile
 65                  70                  75                  80 att atg aag aaa att tta gaa gtt tac aga gga ttc gaa gat gta aat    288
Ile Met Lys Lys Ile Leu Glu Val Tyr Arg Gly Phe Glu Asp Val Asn
                 85                  90                  95 act ttg gtg gat att gga gga gga ctt ggc acc gta cta aac ctt gtc    336
Thr Leu Val Asp Ile Gly Gly Gly Leu Gly Thr Val Leu Asn Leu Val
            100                 105                 110 act tcc aag tat cct caa att aag ggt atc aat ttc gat tta acc atg    384
Thr Ser Lys Tyr Pro Gln Ile Lys Gly Ile Asn Phe Asp Leu Thr Met
        115                 120                 125 gtt tta gcc aat gct cct tct tat cca gga gtg g                      418
Val Leu Ala Asn Ala Pro Ser Tyr Pro Gly Val
    130                 135
```

<210> SEQ ID NO 22
<211> LENGTH: 139
<212> TYPE: PRT
<213> ORGANISM: Brassica napus

<400> SEQUENCE: 22

```
Ala Glu Pro Val Cys Thr Leu Phe Leu Thr Arg Gly Asp Asp Ser Gly
 1               5                  10                  15

Thr His Lys Ser Leu Phe Met Leu Leu Asn Ser Gln Val Phe Phe Lys
             20                  25                  30

Thr Trp Asp Asn Leu Lys Gly Val Ile Gln Glu Gly Lys Asp Ala Phe
         35                  40                  45

Ser Ser Ala His Gly Met Pro Leu Phe Glu Tyr Ile Gly Leu Asp Glu
     50                  55                  60

Gln Phe Ala Gly Met Phe Asn His Ala Met Ala Glu Ser Ser Thr Ile
 65                  70                  75                  80

Ile Met Lys Lys Ile Leu Glu Val Tyr Arg Gly Phe Glu Asp Val Asn
                 85                  90                  95

Thr Leu Val Asp Ile Gly Gly Gly Leu Gly Thr Val Leu Asn Leu Val
            100                 105                 110

Thr Ser Lys Tyr Pro Gln Ile Lys Gly Ile Asn Phe Asp Leu Thr Met
        115                 120                 125

Val Leu Ala Asn Ala Pro Ser Tyr Pro Gly Val
    130                 135
```

<210> SEQ ID NO 23

```
<211> LENGTH: 10
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: VARIANT
<222> LOCATION: (4)
<223> OTHER INFORMATION: E/Q-variation

<400> SEQUENCE: 23

Asn Gly Asp Glu Val Ser Arg Asn Ile Ala
 1               5                  10

<210> SEQ ID NO 24
<211> LENGTH: 9
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: VARIANT
<222> LOCATION: (7)
<223> OTHER INFORMATION: R/K-variation

<400> SEQUENCE: 24

Leu Ala Lys His Gly Cys Arg Leu Val
 1               5

<210> SEQ ID NO 25
<211> LENGTH: 15
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: unsure
<222> LOCATION: (5)
<223> OTHER INFORMATION: All occurrences of Xaa indicate any amino acid

<400> SEQUENCE: 25

Met Gly Asn Glu Xaa Ser Leu Arg Ser Xaa Val Asp Xaa Ile Arg
 1               5                  10                  15

<210> SEQ ID NO 26
<211> LENGTH: 17
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: VARIANT
<222> LOCATION: (14)
<223> OTHER INFORMATION: Q/E-variation

<400> SEQUENCE: 26

Thr Tyr Gln Gly Lys Xaa Gln Asp Ile Leu Xaa Val Ser Gln Asp Glu
 1               5                  10                  15

Phe

<210> SEQ ID NO 27
<211> LENGTH: 17
<212> TYPE: PRT
<213> ORGANISM: Artificial sequence
<220> FEATURE:
<223> OTHER INFORMATION: Description of the artificial sequence: protein
```

```
                                       motif
<220> FEATURE:
<221> NAME/KEY: VARIANT
<222> LOCATION: (3)
<223> OTHER INFORMATION: K/R-variation

<400> SEQUENCE: 27

Ile Thr Lys Ile Asn Leu Thr Ala Xaa Trp Phe Xaa Leu Lys Ala Val
  1               5                  10                  15

Ala

<210> SEQ ID NO 28
<211> LENGTH: 9
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: unsure
<222> LOCATION: (7)
<223> OTHER INFORMATION: All occurrences of Xaa indicate any amino acid

<400> SEQUENCE: 28

Ala Glu Pro Val Cys Thr Xaa Phe Leu
  1               5

<210> SEQ ID NO 29
<211> LENGTH: 16
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: unsure
<222> LOCATION: (5)
<223> OTHER INFORMATION: All occurrences of Xaa indicate any amino acid

<400> SEQUENCE: 29

Glu Gly Lys Asp Xaa Phe Xaa Ser Ala His Gly Met Xaa Xaa Phe Glu
  1               5                  10                  15

<210> SEQ ID NO 30
<211> LENGTH: 11
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: unsure
<222> LOCATION: (5)
<223> OTHER INFORMATION: All occurrences of Xaa indicate any amino acid

<400> SEQUENCE: 30

Glu Gln Phe Ala Xaa Met Phe Asn Xaa Ala Met
  1               5                  10

<210> SEQ ID NO 31
<211> LENGTH: 17
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: VARIANT
<222> LOCATION: (8)
<223> OTHER INFORMATION: V/I-variation
```

```
<220> FEATURE:
<221> NAME/KEY: VARIANT
<222> LOCATION: (13)
<223> OTHER INFORMATION: K/R-variation

<400> SEQUENCE: 31

Ala Thr Xaa Ile Met Lys Lys Val Leu Glu Val Tyr Lys Gly Phe Glu
  1               5                  10                  15

Asp

<210> SEQ ID NO 32
<211> LENGTH: 11
<212> TYPE: PRT
<213> ORGANISM: Artificial sequence
<220> FEATURE:
<223> OTHER INFORMATION: Description of the artificial sequence: protein
      motif
<220> FEATURE:
<221> NAME/KEY: VARIANT
<222> LOCATION: (5)
<223> OTHER INFORMATION: V/I-variation

<400> SEQUENCE: 32

Thr Leu Val Asp Val Gly Gly Gly Xaa Gly Thr
  1               5                  10

<210> SEQ ID NO 33
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 33
cacttttccc ggcaataaca t                                              21

<210> SEQ ID NO 34
<211> LENGTH: 21
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 34
atcaggaagt gatggagcat c                                              21

<210> SEQ ID NO 35
<211> LENGTH: 19
<212> TYPE: DNA
<213> ORGANISM: Artificial sequence
<220> FEATURE:
<223> OTHER INFORMATION: Description of the artificial sequence:
      oligonucleotide primer

<400> SEQUENCE: 35
gaccctgtcc cacctccaa                                                 19

<210> SEQ ID NO 36
<211> LENGTH: 21
<212> TYPE: DNA
```

```
<213> ORGANISM: Artificial sequence
<220> FEATURE:
<223> OTHER INFORMATION: Description of the artificial sequence:
      oligonucleotide primer

<400> SEQUENCE: 36
tgagaactgc gattgtttgc a                                              21
```